(12) United States Patent
Siles et al.

(10) Patent No.: US 8,173,696 B2
(45) Date of Patent: May 8, 2012

(54) INHIBITORS OF CYSTEINE PROTEASES AND METHODS OF USE THEREOF

(75) Inventors: Rogelio Siles, Baltimore, MD (US); Ming Zhou, Coppell, TX (US); J. Freeland Ackley, Erie, PA (US); Kevin G. Pinney, Woodway, TX (US); Shen-En Chen, Waco, TX (US); Wara Milenka Arispe-Angulo, Waco, TX (US); Mary Lynn Trawick, Woodway, TX (US)

(73) Assignee: Baylor University, Waco, TX (US)

( * ) Notice: Subject to any disclaimer, the term of this patent is extended or adjusted under 35 U.S.C. 154(b) by 897 days.

(21) Appl. No.: 12/138,806

(22) Filed: Jun. 13, 2008

(65) Prior Publication Data

US 2009/0076076 A1    Mar. 19, 2009

Related U.S. Application Data

(60) Provisional application No. 60/934,512, filed on Jun. 13, 2007.

(51) Int. Cl.
*A61K 31/382* (2006.01)
(52) U.S. Cl. .................................................. 514/432
(58) Field of Classification Search .................. 514/583, 514/432
See application file for complete search history.

(56) References Cited

U.S. PATENT DOCUMENTS

2004/0014801 A1   1/2004   Cohen et al.

FOREIGN PATENT DOCUMENTS

WO          2005/087211          9/2005

OTHER PUBLICATIONS

Berdowska., "Cysteine proteases as disease markers." Clinica. Chimica. Acta., 2004, vol. 342, pp. 41-69.
Castino et al., "Destination Lysosome : a target organelle for tumour cell killing?" Journal of Molecular Recognition, 2003, vol. 16, pp. 337-348.
Cazzulo., "Proteinases of *Trypanosoma cruzi*: Potential Targets for the Chemotherapy of Chagas Disease." Current Topics in Medicinal Chemistry, 2002, vol. 2, pp. 1261-1271.
Chen et al., "In vivo imaging of proteolytic activity in atherosclerosis." Circulation, Jun. 11, 2002, vol. 105(23), pp. 2766-2771.
Chiyanzu et al., "Synthesis and Evaluation of Isatins and Thiosemicarbazone Derivatives against Cruzain, Falcipain-2 and Rhodesain." Bioorganic & Medicinal Chemistry Letters, 2003, vol. 13, pp. 3527-3530.
Das et al., "Successful therapy of lethal murine visceral leishmaniasis with cystatin involves up-regulation of nitric oxide and a favorable T cell response." J. Immunol., Mar. 15, 2001, vol. 166(6), pp. 4020-4028.
Du et al., "Synthesis and Structure-Activity Relationship Study of Potent Trypanocidal Thio Semicarbazone Inhibitors of the Trypanosomal Cysteine Protease Cruzain." J. Med. Chem., 2002, vol. 45, pp. 2695-2707.
Duthie et al., "Treatment with alpha-galactosylceramide before *Trypanosoma cruzi* infection provides protection or induces failure to thrive." J. immunol., Jun. 1, 2002, vol. 168(11), pp. 5778-5785.
Fujii et al., "Discovery of potent thiosemicarbazone inhibitors of rhodesain and cruzain." Bioorganic & Medicinal Chemistry Letters, 2005, vol. 15, pp. 121-123.
Gillmor et al., "Structural determinants of specificity in the cysteine protease cruzain." Protein Science, 1997, vol. 6, pp. 1603-1611.
Gottesman., "Cathepsin L and cancer." Proteolysis and Protein Turnover, Proc. 9th ICOP Meeting, Williamsburg, VA, 1993, pp. 247-251.
Greenbaum et al., "Synthesis and Structure-Activity Relationships of Parasiticidal Thiosemicarbazone Cysteine Protease Inhibitors against *Plasmodium falciparum*, *Trypanosoma brucei*, and *Trypanosoma cruzi*." J. Med. Chem., 2004, vol. 47., pp. 3212-3219.
Guarner et al., "Mouse model for Chagas disease: immunohistochemical distribution of different stages of *Trypanosoma cruzi* in tissues throughout infection." Am. J. Trop. Med. Hyg., Aug. 2001, vol. 65(2), pp. 152-158.
Jedinak et al., "Inhibitors of proteases as anticancer drugs." Neoplasma, 2005, vol. 52, No. 3, pp. 185-192.
Joachimiak et al., "The Impact of whole genome sequence data on drug discovery—a malaria case study." Mol. Med., Oct. 2001, vol. 7(10), pp. 698-710.
Kane et al., "The role of cathepsin L in malignant transformation." seminars in Cancer Biology, 1990, vol. 1, pp. 127-136.
Kirschke., "Lysosomal Cysteine Peptidases and Malignant Tumours." Cellular Peptidases in Immune Functions and Diseases, edited by Ansorge and Langer, Plenum Press, New York, 1997, pp. 253-257.
Kobayashi et al., "Inhibition of in vitro ovarian cancer invasion by modulation of urokinase-type plasminogen activator and cathepsin B." Cancer Res., Jul. 1, 1992, vol. 52(13), pp. 3610-3614.
Krueger et al., "Inhibitory effects of antisense cathepsin B cDNA transfection on invasion and motility in a human osteosarcoma cell line." Cancer Res., Dec. 1, 1999, vol. 59(23), pp. 6010-6014.
Mohamed et al., "Cysteine cathepsins: multifunctional enzymes in cancer." Reviews, Oct. 2006, vol. 6, pp. 764-775.
Mucci et al., "Thymocyte depletion in *Trypanosoma cruzi* infection is mediated by trans-sialidase-induced apoptosis on nurse cells complex." Pro. Natl. Acad. Sci., Mar. 19, 2002, vol. 99(6), pp. 3896-3901.
Rhee et al., "Vaccination with heat-killed leishmania antigen or recombinant leishmanial protein and CpG oligodeoxynucleotides induces long-term memory CD4+ and CD8+ T cell responses and protection against leishmania major infection." J. Exp. Med., Jun. 17, 2002, vol. 195(12), pp. 1565-1573.
Selzer et al., "Cysteine protease inhibitors as chemotherapy: lessons from a parasite target." Proc. Natl. Acad. Sci., Sep. 28, 1999, vol. 96(20), pp. 11015-11022.
Semenov et al., "Antimalarial synergy of cysteine and aspartic protease inhibitors." Antimicrob. Agents Chemother., Sep. 1998, vol. 42(9), pp. 2254-2258.

(Continued)

*Primary Examiner* — Taofiq A Solola
(74) *Attorney, Agent, or Firm* — Karen E. Flick

(57) ABSTRACT

The present invention relates to semicarbazone or thiosemicarbazone inhibitors of cysteine proteases and methods of using such compounds to prevent and treat protozoan infections such as trypanosomiasis, malaria and leishmaniasis. The compounds also find use in inhibiting cysteine proteases associated with carcinogenesis, including cathepsins B and L.

19 Claims, No Drawings

OTHER PUBLICATIONS

Sijwali et al., "Expression and characterization of the *Plasmodium falciparum* haemoglobinase falcipain-3." Biochem. J., Dec. 1, 2001, vol. 360(pt 2), pp. 481-489.

Siles et al., "Design, synthesis, and biochemical evaluation of novel cruzain inhibitors with potential application in the treatment of Chagas' disease." Bioorg. Med. Chem. Lett., 2006, vol. 16, pp. 4405-4409.

Simmons et al., "Inhibitors of cathepsin L prevent severe acute respiratory syndrome coronavirus entry." PNAS, Aug. 16, 2005, vol. 102, No. 33, 11876-11881.

Singh et al., "Comparison of efficacies of cysteine protease inhibitors against five strains of *Plasmodium*." Antimicrob. Agents Chemother., Mar. 2001, vol. 45(3), pp. 949-951.

Skrzdlewska et al., "Proteolytic-antiproteolytic balance and its regulation in carcinogenesis." World Journal of Gastroenterology, 2005, vol. 11, No. 9, pp. 1251-1266.

Urbina., "Chemotherapy of Chagas Disease." Current Pharmaceutical Design, 2002, vol. 8, pp. 287-295.

Zuniga et al., "*Trypanosoma cruzi* infection selectively renders parasite-specific IgG+B lymphocytes susceptible to Fas/Fas ligand-mediated fratricide." J. Immunol., Apr. 15, 2002, vol. 168(8), pp. 3965-3973.

Zwicky et al., "Cathepsin B expression and down-regulation by gene silencing and antisense DNA in human chondrocytes." Biochem. J., Oct. 1, 2002, vol. 367(Pt 1), pp. 209-217.

Shen-En Chen, "Design, Synthesis and Biochemical Evaluation of Cysteine Protease Inhibitors: Novel Componds for Chagas Treatment." Poster Presented Jul. 10, 2005, NATEA, Dallas/Ft. Worth Airport Marriott South.

Sites et al., "Design, Synthesis and Biochemical Evaluation of Cysteine Protease Inhibitors: Novel Compounds for Chagas' Treatment." Poster Presented at National Meeting of the American Chemical Society in San Diego, CA, Mar. 16, 2005.

INHIBITORS OF CYSTEINE PROTEASES AND METHODS OF USE THEREOF

RELATED APPLICATION

This application claims priority to U.S. Provisional Application Ser. No. 60/934,512, entitled "Inhibitors of Cysteine Proteases and Methods of Use", filed on Jun. 13, 2007. The entire contents of the aforementioned application are hereby incorporated herein by reference.

BACKGROUND OF THE INVENTION

A major class of proteases involved in the etiology of disease are the cysteine proteases. Cysteine proteases share a common proteolytic mechanism that requires a nucleophilic cysteine thiol in the active site of the protease. Examples of cysteine proteases include caspases, which are essential for mediating cellular apotosis, and calpains, a group of calcium-dependent, non-lysosomal cysteine proteases that are involved in a variety of diseases, including cancer. Other important cyteine proteases involved in disease are the cathepsins. Most cathepsins reside in lysosomes where they are activiated by acidic pH. Cathepsins play a vital role in the turnover of cellular proteins. For example, cathepsin L is a major lysosomal protease that is synthesized as a proenzyme and is secreted from cells where it is activated and promotes the degradation of the extracellular matrix and basement membrane required for tumor metastasis. Increased cathepsin L activity is linked to invasive and metastatic cancers including prostate, colorectal and melanoma cancers. This major cysteine protease also plays a role in the pathology of degenerative cartilage and bone disorders such as rheumatoid arthritis, and osteoporosis, and neurological disorders including Alzheimer's. Cathepsin L activity is also reported to be required for SARS coronavirus infection.

In view of the important role of cysteine proteases in mediating a variety of diseases, there is an urgent need to develop potent, efficacious, and pharmaceutically acceptable compounds capable of inhibiting the activity of these proteases.

SUMMARY OF THE INVENTION

The present invention relates to thio semicarbazone and semicarbazone compounds, and cyclized pyrazoline analogues of either, that function as cysteine protease inhibitors and the use of such compounds in methods of treating and preventing diseases associated with cysteine proteases.

The compounds are exemplified by a structural scaffold of the chemical formula I:

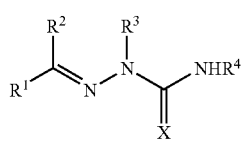
(I)

and pharmaceutically acceptable salts, enantiomers, stereoisomers, rotamers, tautomers, diastereomers, or racemates thereof;

wherein $R^1$ and $R^2$ are each, independently, selected from the group consisting of substituted or unsubstituted phenyl; or $R^1$ and $R^2$ may together form a substituted or unsubstituted 5- or 6-membered alicyclic or heterocyclic, or a 9- or 10-membered fused bi-alicyclic or bi-heterocyclic;

$R^3$ is selected from the group consisting of H, and substituted or unsubstituted lower alkyl, $R^4$ is a member selected from H and substituted or unsubstituted lower alkyl; and X is O or S.

In one embodiment of Formula I, $R^1$ and $R^2$ are each, independently,

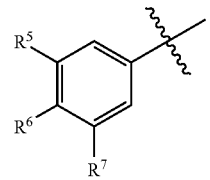

wherein $R^5$, $R^6$, and $R^7$ are each, independently, selected from the group consisting of H, substituted or unsubstituted alkyl, substituted or unsubstituted aryl, substituted or unsubstituted heteroaryl, haloalkyl, alkoxy, $NO_2$, $NH_2$, OH, N-acyl and halo. In another embodiment, $R^5$, $R^6$ and $R^7$ are each, independently, selected from the group consisting of H, halo and haloalkyl. In still another embodiment, $R^5$, $R^6$ and $R^7$ are each, independently, selected from the group consisting of $NO_2$, $NH_2$, OH and halo.

In one embodiment of Formula I, $R^1$ and $R^2$ together form a substituted or unsubstituted cyclobutyl, a substituted or unsubstituted cyclopentyl, or substituted or unsubstituted cyclohexyl group, or $R^1$ and $R^2$ together form a substituted or unsubstituted 9- or 10-membered fused bi-alicyclic or bi-heterocyclic of the Formulae A or B:

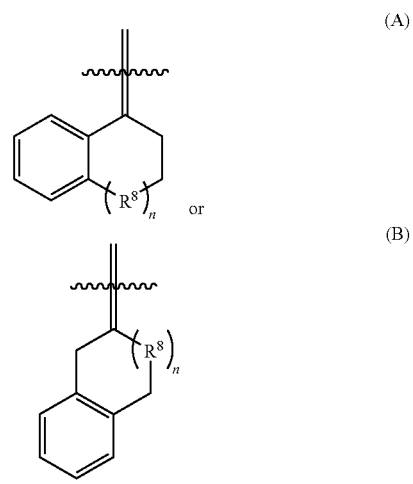

wherein n is 0 or 1; and $R^8$ is selected from the group consisting of $CH_2$, S, O and $SO_2$. In another embodiment, when $R^1$ and $R^2$ together form a cyclobutyl, cyclopentyl, or cyclohexyl group, which can be further independently substituted one or more times with phenyl, $NO_2$, $NH_2$, OH or halo, wherein the phenyl group may be further substituted with $NO_2$, $NH_2$, OH or halo. In another embodiment, $R^1$ and $R^2$ together form substituents of the Formulae A or B, which may be substituted one or more times with phenyl, $NO_2$, $NH_2$, OH or halo, wherein the phenyl group may be further substituted with $NO_2$, $NH_2$, OH or halo.

In another embodiment of Formula I, $R^3$ is H. In still another embodiment, X is S. In yet another embodiment, $R^4$ is H.

In a particular embodiment of Formula I, $R^4$ is H, X is S, and $R^3$ is H. In another embodiment of Formula I, $R^4$ is H, X is S, $R^3$ is H, and $R^1$ and $R^2$ are both phenyl substituted one or more times with bromo. In another embodiment of Formula I, $R^4$ is H, X is S, $R^3$ is H, and $R^1$ and $R^2$ together form a thiochroman 1,1-dioxide ring, which may be substituted one or more times with bromo.

In a particular embodiment of the variable definitions given above, halo is Br.

Preferably, the compounds inhibit a target cysteine protease of interest with a potency or IC50 value of less than 1000 nanomolar (nM), more preferably of less than about 500, 300 or 100 nM, and most preferably less than about 80, 70, 60, 50, 40, 30, 20, or 10 nM.

In one aspect, the compounds are provided as part of a pharmaceutical composition. An exemplified pharmaceutical composition includes at least one compound such as a thio semicarbazone, or a semicarbazone analogue of either, in a pharmaceutically acceptable carrier, such that administration of the composition to an individual would render the one or more compounds sufficiently bioavailable to effectively inhibit a target cysteine protease.

Exemplary compounds, which find particular use in a pharmaceutical composition of the invention, include those of Tables A and B, shown below.

In one aspect, the present invention relates to a method for inhibiting a cysteine protease involved in the infectious life cycle of a protozoan parasite, the method comprising the step of administering to the subject a pharmaceutical composition comprising a pharmaceutically acceptable carrier and a compound that inhibits such a cysteine protease, said composition administered to the subject in an amount sufficient to inhibit the target cysteine protease and disrupt the infectious life cycle of a protozoan parasite, wherein the compound forms a reversible covalent association with a cysteine in the active site of the target cysteine protease.

In another aspect the present invention relates to a method for treating or preventing a protozoan parasitic disease or infection, the method comprising the step of administering to the subject a pharmaceutical composition comprising a pharmaceutically acceptable carrier and a compound that inhibits a cysteine protease required in the infectious life cycle of the protozoan parasite, said composition administered to the subject in an amount sufficient to inhibit the target cysteine protease and disrupt the infectious life cycle of a protozoan parasite thereby treating or preventing a protozoan parasitic disease or infection in the subject.

Exemplary protozoan cysteine proteases include those required in the infectious life cycle of a trypanosome, such as cruzain or cruzipain from *T. cruzi*, rhodesain or brucipain from *T. brucei rhodesiense*, and congopain from *T. congolense*; a plasmodium, such as falcipain from *P. falciparum*; or a leishmania, such as CPB2.8 Delta CTE from *L. mexicana*.

In one embodiment, the cysteine protease is a cathepsin L-like protease.

In one embodiment, the cysteine protease is a cathepsin B-like protease. In one embodiment, the protozoan parasite is a *Trypanosoma*, a *Plasmodium* or a *Leishmania*. In a further embodiment, the parasite is selected from the group consisting of *Trypanosoma cruzi, Trypanosoma brucei gambiense, Trypanosoma brucei rhodesiense, Trypanosoma rangeli, Trypanosoma congolense, Plasmodium falciparum, Plasmodium malariae, Plasmodium vivax, Plasmodium ovale, Leishmania major, Leishmania braziliensis, Leishmania mexicana, Leishmania donvani, Leishmania pifanoi* and *Leishmania tropica*.

In one embodiment the parasitic disease is selected from the group consisting of Chagas' disease, African sleeping sickness, nagana, malaria, and leishmaniasis (cutaneous, mucocutaneous or visceral).

In one aspect, the invention relates to a method of inhibiting a mammalian cysteine protease involved in the malignancy of a cancer cell, the method comprising the step of administering to an individual in need thereof a composition comprising a pharmaceutically acceptable carrier and a compound that inhibits the mammalian cysteine protease by forming a reversible covalent association with a cysteine in the active site of the target cysteine protease.

In one embodiment, the cancer a breast cancer, an oral cancer, a skin cancer, a lung cancer, an intestinal cancer, a bladder cancer or a prostate cancer. In a further embodiment, the cancer is a breast carcinoma, an oral squamous cell carcinoma, a melanoma, a transitional cell carcinoma of the bladder, an intestinal adenoma, a colorectal carcinoma, a neuroblastoma or a prostate carcinoma. In another embodiment, the cancer is a metastatic cancer.

In another aspect, the invention relates to a method of inhibiting a mammalian cysteine protease involved in an inflammatory disease, the method comprising the step of administering to an individual in need thereof a composition comprising a pharmaceutically acceptable carrier and a compound that inhibits the mammalian cysteine protease by forming a reversible covalent association with a cysteine in the active site of the target cysteine protease.

In one embodiment the inflammatory disease is rheumatoid arthritis, atherosclerosis, vascular inflammation, allergic lung inflammation or multiple organ failure.

In another embodiment, the invention relates to a method of inhibiting a mammalian cysteine protease involved in osteoporosis with a compound of the invention.

In another embodiment, the invention relates to a method of inhibiting a neurological disorder, e.g., Alzheimer's. In another embodiment, the invention relates to a method of inhibiting a SARS coronavirus infection.

In one embodiment, the mammalian cysteine protease is a cathepsin L, a cathepsin B, a cathepsin H or a cathepsin K.

In one embodiment, the subject or individual is a mammal. In a further embodiment, the mammal is human, primate, canine, feline, equine, bovine, ovine, porcine, murine or lagomorpha.

In one embodiment, the one or more compounds inhibit a target cysteine protease without inducing toxicity in a host cell or host tissue infected with a protozoan whose infectious life cycle requires the activity of the target protease or in a non-malignant host cell or host tissue that does not express a cysteine protease associated with a malignant cancer cell. Generally, the compounds form a reversible covalent interaction with a cysteine in the active site of a target cysteine protease as part of their inhibitory mechanism.

In one embodiment, the compounds are at least one of Trypanocidal, Plasmodiumcidal, and Leishmaniacidal.

In one embodiment, the compounds are at least one of Trypanostatic, Plasmodiumstatic, and Leishmaniastatic.

DETAILED DESCRIPTION OF THE INVENTION

Cysteine proteases are known to bind to their protein substrates through antiparallel beta sheet structures. The discovery of the improved and potent cysteine protease inhibitors of the invention has resulted from the judicious extension of the thiosemicarbazone functionality into rigid carbon skeletons which mimic the beta sheet conformation of the substrates of these proteases and conform well to their relatively rigid active sites (McGrath, et al. *J. Mol. Biol.* (1995), 247: 251-259; Gillmor, et al., *Protein Science*, (1997), 6: 1603-1611; Choe, et al., *Bioorg. Med. Chem. Lett.* (2005), 13: 2141-2156; and Huang et al., *Bioorg. Med. Chem.* (2003), 11: 21-29). Indeed, the compounds of the invention are surprisingly potent inhibitors of cysteine protease inhibition, with $IC_{50}$ values at the low nanomolar level (e.g., 10 nM or less). Accordingly, the compounds of the invention may be employed in the treatment of parasitic disease states such as malaria, leishmaniasis and trypanosomiasis (e.g., Chagas' disease) as inhibitors of parastic cysteine proteases, including the cathepsin-L like cysteine proteases (e.g., cruzain). Moreover, the compounds of the invention also find use in the treatment of other mammalian disorders (e.g., cancer and inflammatory disorders) as inhibitors of related mammalian cysteine proteases, including cathepsin L, cathepsin B, cathepsin H, cathepsin K and cathepsin S.

Definitions

The terms "cysteine protease" or "cysteine proteinase" or "cysteine peptidase" intend any enzyme of the sub-subclass EC 3.4.22, which consists of proteinases characterized by having a cysteine residue at the active site and by being irreversibly inhibited by sulfhydryl reagents such as iodoacetate. Mechanistically, in catalyzing the cleavage of a peptide amide bond, cysteine proteases form a covalent intermediate, called an acyl enzyme, that involves a cysteine and a histidine residue in the active site (Cys25 and His159 according to papain numbering, for example). Cysteine protease targets of particular interest in the present invention belong to the family C1 within the papain-like clan CA. Representative cysteine protease targets for the present invention include papain, cathepsin B (EC 3.4.22.1), cathepsin H (EC 3.4.22.16), cathepsin L (EC 3.4.22.15), cathepsin K, cathepsin S (EC 3.4.22.27), cruzain or cruzipain, rhodesain, brucipain, congopain, falcipain and CPB2.8 Delta CTE. Preferred cysteine protease targets of the present invention cleave substrate amino acid sequences -Phe-Arg-|-Xaa-, -Arg-Arg-|-Xaa-, -Val-Val-Arg-|-Xaa- or -Gly-Pro-Arg-|-Xaa-. Clan CA proteases are characterized by their sensitivity to the general cysteine protease inhibitor, E64 (L-trans-epoxysuccinyl-leucyl-amido (4-guanidino) butane) and by having substrate specificity defined by the $S_2$ pocket.

Cysteine proteases inhibited by the compounds of the present invention can be "cathepsin L-like" or "cathepsin B-like." A cathepsin L-like cysteine protease shares structural and functional similarity with a mammalian cathepsin L, and comprises a "ERFNIN" motif (Sajid and McKerrow, supra). Cathepsin L-like cysteine proteases prefer as a substrate the dipeptide sequence -Phe-Arg-|-Xaa-. Representative cathepsin L-like cysteine proteases include cathepsin L, cathepsin K, cathepsin S, cruzain, rhodesain and congopain, *T. cruzi*-L, *T. rangeli*-L, *T. congolense*-L, *T. brucei*-L, *P. falciparum*-L1, *P. falciparum*-L2, *P. falciparum*-L3, *P. vivax*-L1, *P. cynomolgi*-L1, *P. vinckei*-L and *L. major*-L. A cathepsin B-like cysteine protease shares structural and functional similarity with a mammalian cathepsin B, and comprises an "occluding loop" (Sajid and McKerrow, supra). Cathepsin B-like cysteine proteases cleave as a substrate the dipeptide sequences -Arg-Arg-|-Xaa- and -Phe-Arg-|-Xaa-. Representative cathepsin B-like proteases include cathepsin B, *T. cruzi*-B, *L. mexicana*-B and *L. major*-B.

"Inhibitors" or "inhibition" of cysteine proteases refers to inhibitory compounds identified using in vitro and in vivo assays for cysteine protease function. In particular, inhibitors refer to compounds that decrease or obliterate the catalytic function of the target cysteine protease, thereby interfering with or preventing the infectious life cycle of a parasite or the migratory capacity of a cancer cell or an inflammatory cell. In vitro assays evaluate the capacity of a compound to inhibit the ability of a target cysteine to catalyze the cleavage of a test substrate. Cellular assays evaluate the ability of a compound to interfere with the infectious life cycle of a parasite or the migration of a cancer or inflammatory cell ex vivo, while not exhibiting toxicity against the host cell. Cellular assays measure the survival of a parasite-infected cell in culture. Preferred inhibitors allow for extended survival of an infected cell, either by delaying the life cycle of the parasite, or by killing the parasite. In vivo assays evaluate the efficacy of test compounds to prevent or ameliorate disease symptoms, such as those associated with parasitic infection, cancer invasion or growth, or inflammatory cell migration. Inhibitors are compounds that eliminate or diminish the catalytic function of a cysteine protease. Further, preferred inhibitors delay, interfere with, prevent or eliminate the completion of the infectious life cycle of a parasite or the migratory ability of a cancer cell or an inflammation cell. Additionally, preferred inhibitors prevent or diminish a parasitic infection in an individual or the migration of cancer cells or inflammatory cells in an individual, thereby preventing or ameliorating the pathogenic symptoms associated with such infections or the migration of rogue cells.

To examine the extent of inhibition, samples, assays, cultures or test subjects comprising a target cysteine protease are treated with a potential inhibitor compound and are compared to negative control samples without the test compound, and positive control samples, treated with a compound known to inhibit the target cystein protease. Negative control samples (not treated with a test compound), are assigned a relative cysteine protease activity level of 100%. Inhibition of a cysteine protease is achieved when the cysteine protease activity relative to the control is about 90%, preferably 75% or 50%, more preferably 25-0%.

An amount of compound that inhibits a cysteine protease, as described above, is an amount sufficient to inhibit a "cysteine protease," or a "cysteine protease inhibiting amount" of compound, thereby preventing or treating a parasitic infection, inflammation, or cancer invasion or growth in an individual.

The term "$IC_{50}$" refers to the concentration of compound that results in half-maximal inhibition of enzyme.

By "parasitistatic" or "trypanostatic" or "*plasmodium*-static" or "*leishmania*-static" is intended that the intracellular cycle of the parasite is completed at a slower growth rate and the infected host cells survive longer.

The term "parasiticidal" or "trypanocidal" or "*plasmodium*-cidal" or "*leishmania*-cidal" means that the intracellular cycle of the parasite is not completed, therefore, leading to the death of the parasites.

For the thio semicarbazone compounds of the invention, the term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is meant to include "alkylene." The term "alkyl," unless otherwise noted, is also meant to include those derivatives of alkyl defined in more detail below as "heteroalkyl." (e.g., "alkoxy," "alkylamino" and "alkylthio"). Alkyl groups which are limited to hydrocarbon groups are termed "homoalkyl."

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2 m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)

=NH, —NR'C(NH$_2$)=NH, —NH—C(NH$_2$)=NR', —S(O)R', —S(O)$_2$R', —S(O)$_2$NR'R'', —N3, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds of the Invention

The present invention provides compounds that can be used for the treatment of a variety of diseases and disorders, including parasitic diseases or parasitic infections, as well as cancer. The compounds of the invention are also useful for the inhibition of a cysteine protease, including mammalian cysteine proteases involved in the malignancy of a cancer cell.

In one aspect, the compound of the invention is of the Formula I:

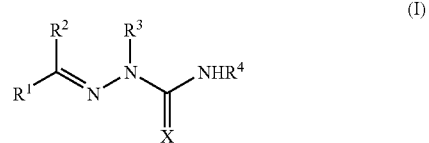

(I)

and pharmaceutically acceptable salts, enantiomers, stereoisomers, rotamers, tautomers, diastereomers, or racemates thereof; wherein the variables of Formula I are as defined above.

Certain exemplary compounds of the invention (i.e., compounds of the Formula I) are listed below in Tables A and B, are referred to by the compound number as indicated, and are also referred to as "compounds of the invention." The species listed include all pharmaceutically acceptable salts, polymorphs, enantiomers, stereoisomers, rotamers, tautomers, diastereomers, or racemates thereof. Synthesis procedures for these compounds, as well as procedures used to acquire the IC$_{50}$'s of these compounds are described in the examples.

TABLE A

| Compound | Structure | Cruzain IC50 (nM) | Cat L IC50 (nM) | Cat B IC50 (nM) |
| --- | --- | --- | --- | --- |
| 13 | 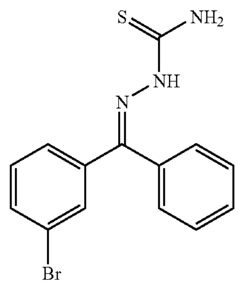 | 80 | 16200 | |
| 14 | 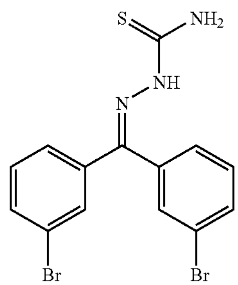 | 24 | 1.5 | >3,000 |
| 38 | 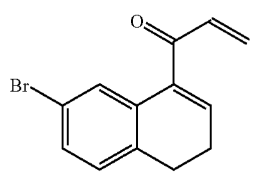 | 802 | 372 | |
| 6 | 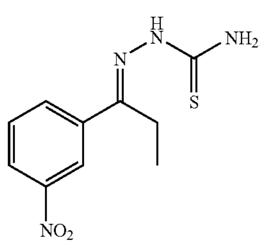 | 860 | 5790 | |
| 8 | 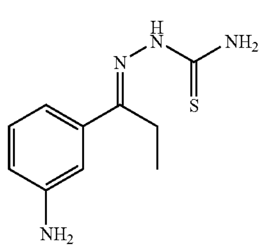 | 3640 | 1640 | |
| 7 | 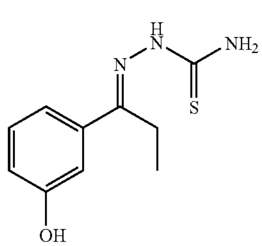 | >33,000 | 2570 | |

TABLE A-continued

| Compound | Structure | Cruzain IC50 (nM) | Cat L IC50 (nM) | Cat B IC50 (nM) |
|---|---|---|---|---|
| 25 | 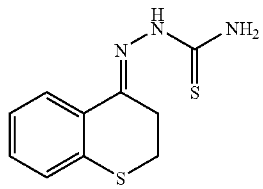 | >2,000 | 983 | >50,000 |
| 21 | 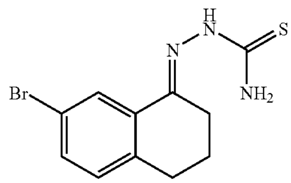 | 17 | 619 | |
| 22 | 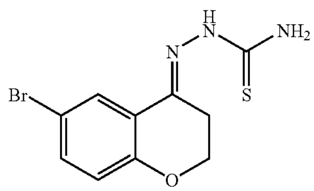 | 110 | 530 | >50,000 |
| 20 | 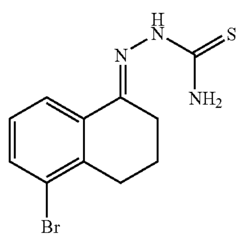 | 1200 | 367 | |
| 37 | 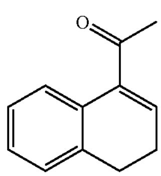 | 1360 | >10000 | |
| 70 | 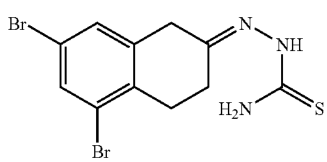 | 4480 | 10900 | >50,000 |
| 46 | 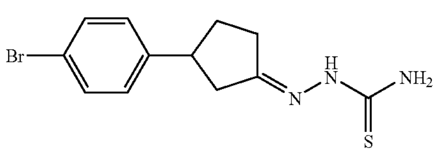 | >5,000 | >10000 | NDA |
| 47 | 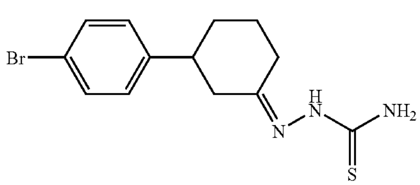 | >7,000 | 2910 | NDA |

TABLE A-continued

| Compound | Structure | Cruzain IC50 (nM) | Cat L IC50 (nM) | Cat B IC50 (nM) |
|---|---|---|---|---|
| 26 | 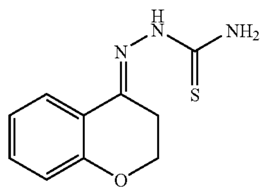 | >17,000 | 6380 | |
| 48 | 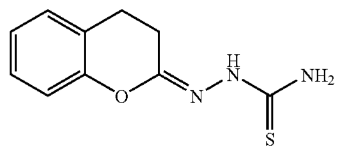 | >17000 | 2450 | |
| 41 | 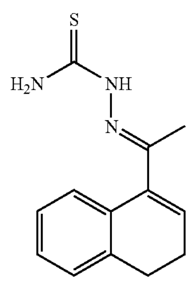 | >20,000 | >10000 | |
| 49 | 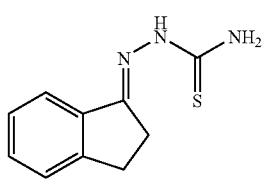 | >17,000 | >10000 | |
| 69 | 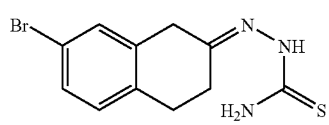 | >17,000 | 4260 | <50,000 |
| 24 | 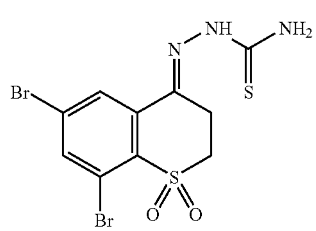 | 820 | 716 | |
| 23 | 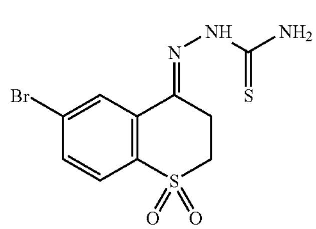 | 210 | 1.0 | |

TABLE A-continued

| Compound | Structure | Cruzain IC50 (nM) | Cat L IC50 (nM) | Cat B IC50 (nM) |
|---|---|---|---|---|
| 27 | 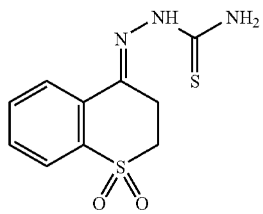 | >20,000 | 5050 | |
| 38 | 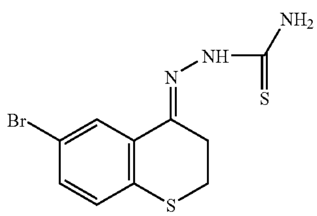 | | | |
| 59 | 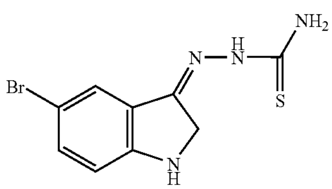 | | | |
| 60 | 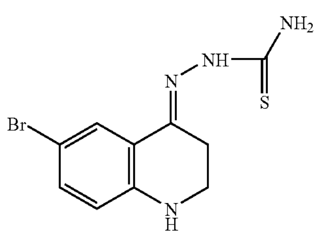 | | | |
| 61 | 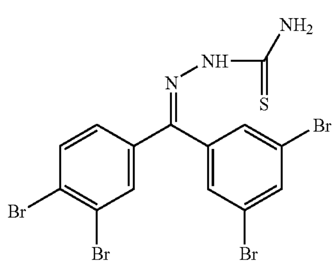 | | | |
| 62 | 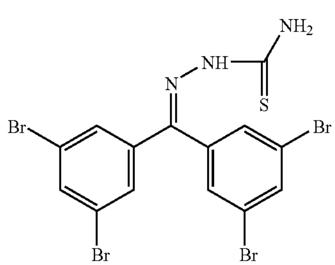 | | | |

TABLE A-continued
| Compound | Structure | Cruzain IC50 (nM) | Cat L IC50 (nM) | Cat B IC50 (nM) |
|---|---|---|---|---|
| 63 | 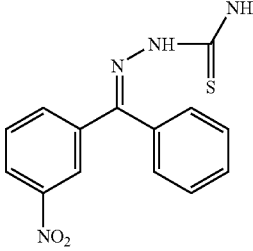 | | | |
| 64 | 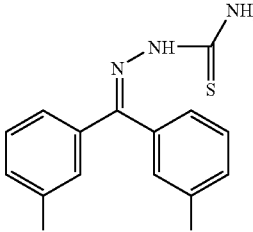 | | | |
| 65 | 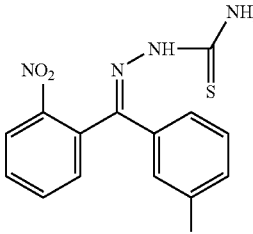 | | | |
| 66 | 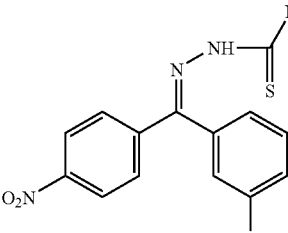 | | | |
| 67 | 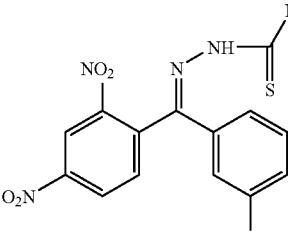 | | | |
| 68 | 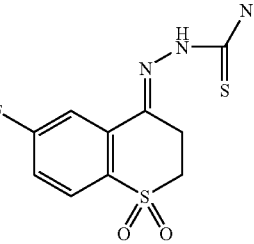 | | | |

TABLE A-continued

| Compound | Structure | Cruzain IC50 (nM) | Cat L IC50 (nM) | Cat B IC50 (nM) |
|---|---|---|---|---|
| 71 | 3,5-dibromophenyl / 3-bromophenyl ketone thiosemicarbazone | | | |
| 72 | 3,5-dibromophenyl / 3,4-dibromophenyl ketone thiosemicarbazone | | | |
| 73 | 3-aminophenyl / 3-bromophenyl ketone thiosemicarbazone | | | |
| 74 | 3-hydroxyphenyl / 3-bromophenyl ketone thiosemicarbazone | | | |
| 75 | 3-(N-Acyl)phenyl / 3-bromophenyl ketone thiosemicarbazone | | | |

TABLE B

| Compound | Structure | Cruzain | Cat L | Cat B |
|---|---|---|---|---|
| 5 | (3-bromophenyl ethyl thiosemicarbazone) | 240 | >10000 | >50,000 |

Preparation of Thio Semicarbazone and Semicarbazone Inhibitors of Cysteine Proteases Thio Semicarbazones and Semicarbazones can be synthesized according to Scheme 1. Refluxing aldehyde or ketone with a thio semicarbazide generates thio semicarbazones. For aldehydes, the reaction is usually complete in less than 3 h and no acetic acid is required. For ketones, the reaction is usually run overnight with 1% acetic acid. Yields are generally greater than 90% except with a few specific ketones such as the 2-substituted aryl ketones. Synthesis of semicarbazones is done at room temperature. A sodium acetate solution of semicarbazide hydrochloride salt is added to the ethanol solution of aldehyde or ketone (Pandeya, S, N. et al., Pharmacol Res., 37:17-22 (1998)). The product usually precipitates out with good yield.

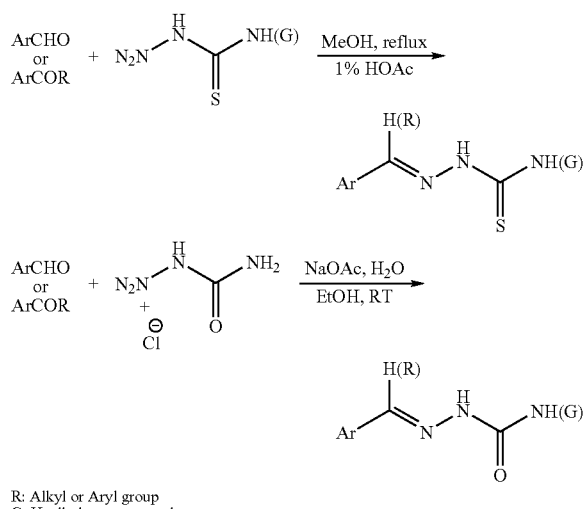

R: Alkyl or Aryl group
G: H, alkyl group, or aryl group

Additional synthesis procedures are described in the examples.

Methods of Treating Cysteine Protease-Related Disorders (a) Treatment of Disorders associated with Parisitic Cysteine Proteases In certain embodiments, methods of treating parasitic disorders with the compounds of the invention are provided.

In one embodiment, the compounds of the invention may be employed in the treatment of Chagas' disease. Chagas' disease is transmitted to humans by blood-sucking triatomine vectors with an infectious trypomastigote form of the protozoan parasite *T. cruzi* (Bonaldo, M. C. et al., Exp. Parasitol, 73:44-51 (1981); Harth, G., et al., *T. Cruzi*. Mol. Biochem Parasitol, 58:17-24 (1993); Meirelles, M. N. L., et al., Mol. Biochem. Parasitol, 52:175-184 (1992)). The primary cysteine protease, cruzain or cruzipain, is essential for infection of host cells, replication and metabolism throughout the life cycle of the *T. cruzi* parasite. Accordingly, inhibition of cruzain is thought to be an effective strategy for cure this infection.

In another embodiment, the compounds of the invention may be employed in the treatment of African trypanosomiasis. African trypanosomiasis is transmitted to humans and cattle by tsetse flies and is caused by subspecies of *T. brucei*. So called "African sleeping sickness" is transmitted by an infectious trypomastigote from *T. brucei gambiense*, and *T. brucei rhodesiense* produces a progressive and usually fatal form of disease marked by early involvement of the central nervous system. *T. brucei* is further the cause of nagana in cattle, but bovine trypanosomiasis is also transmitted by *T. congolense* and *T. evansi*. In trypanosomiasis infections, the trypomastigote enters the host bloodstream and ultimately invades a cardiac muscle cell, where it transforms into the intracellular amastigote. The parasite may also be found in the blood, lymph, spinal fluid and cells of the gastrointestinal tract. Amastigotes replicate within cells, transform back to trypomastigotes, and rupture the cell, releasing the infectious form back into the bloodstream and other cells, amplifying the infection. Cruzain (also referred to as cruzipain) is the major cysteine protease of *T. cruzi*. The protease is expressed in all life cycle stages of the parasite, but delivered to different cellular compartments in each stage. In the epimastigote stage, which occurs in the insect vector, the protease is in a lysosomal compartment where it functions to degrade proteins endocystosed from the insect gut. In the infectious trypomastigote stage, the protease appears at the flagellar pocket, the site of endocytosis and secretion. In the amastigote stage, within the mammalian host cell, the protease is both in the lysosomal compartment and on the surface of the parasite where it may function in nutrition, remodeling of the mammalian cell, or evasion of host defense mechanisms. Administration of cruzain inhibitors is thought to be a valid strategy for blocking the replication and differentiation of the parasite and thereby arresting the parasite life cycle (McKerrow, J. H. et al., Bioorg. Med. Chem., 7:639-644 (1999)).

In another embodiment, the compounds of the invention may be employed in the treatment of malaria. Malaria is caused by protozoa of the genus *Plasmodium* and is transmitted to humans through the bite of an infected anopheline mosquito. The parasites develop into tissue schizonts in hepatic parenchymal cells, and then are released into the circulation as merozoites, which invade erythrocytes. In erythrocytes, the merozoites mature from trophozoites into schizonts. Schizont-containing erythrocytes rupture to release merozoites that then invade more erythrocytes to continue the malarial cycle. The majority of malaria infections is caused by *Plasmodium falciparum*. Papain-family cysteine proteases, known as falcipains, are hemoglobinases from *P. falciparum* that are essential to *plasmodium* trophozoite protein synthesis and development (Sijwali, et al (2001) Biochem J360:481). Sequencing of the *Plasmodium* genome has revealed at least three falcipain cysteine proteases, designated falcipain-1, falcipain-2 and falcipain-3, where falcipain-2 and falcipain-3 are understood to account for the majority of hemoglobinase activity in the *plasmodium* trophozoite (Joachimiak, et al (2001) Mol. Med 7:698). The falcipains are homologous to cruzain (Venturini, et al (2000) Biochem Biophys Res Commun 270:437 and Selzer, et al (1997) Exp Parasitol 87:212) and at least the falcipain-2 sequence is highly conserved amongst different *Plasmodium* strains with different sensitivities to established antimalarial drugs (Singh and Rosenthal (2001) Antimicrob Agents Chemother 45:949). In in vitro studies, cysteine protease inhibitors blocked globin hydrolysis in *Plasmodium* infected erythrocytes (Rosenthal (1995) Exp. Parasitol 80:272 and Semenov et al (1998) Antimicrob Agents Chemother 42:2254). Importantly, oral or parenteral administration of fluoromethyl ketone or vinyl sulfone peptidyl inhibitors of falcipain cured treated mice that were infected with *Plasmodium* (Olson, et al (1999) Bioorg Med Chem 7:633). Therefore, the falcipains and other homologous cysteine proteases are also important antimalarial chemotherapeutic targets.

In yet another embodiment, the compounds of the invention may be employed in the treatment of leishmaniasis. Leishmaniasis is caused by protozoal species and subspecies of *Leishmania* transmitted to humans by the bites of infected female phlebotamine sandflies. Promastigotes injected into the host are phagocytized by tissue monocytes and are transformed into amastigotes, which reside in intracellular phagolysosomes. Human leishmaniasis is classified into cutaneous, mucocutaneous and visceral (kala azar) forms. In vitro and in vivo studies also have demonstrated that cysteine protease inhibitors disrupt the infectious life cycle of *Leishmania* (see, Selzer, et al (1999) Proc Natl Acad Sci 96:11015; Das, et al (2001) J. Immunol 166:4020 and Salvati, et al (2001) Biochim Biophys Acta 1545:357). Like *Trypanosoma* and *Plasmodium*, *Leishmania* synthesize cathepsin-L-like cysteine proteases that are essential to their pathogenicity (Selzer, et al (1997) Exp Parasitol 87:212). The substrate recognition of one cysteine protease of *L. mexicana*, named CPB2.8 Delta CTE, has been demonstrated to be similar to the substrate preferences of cruzain (Alves, et al (2001) Mol Biochem Parasitol 117:137 and Alves, et al (2001) Mol Biochem Parasitol 116:1). Additionally, cruzain shares sequence similarity with homologous cysteine proteases from *L. pifanoi, L. mexicana*, and *L. major* (see Mottram, et al (1992) Mol Microbiol 6:1925, Rafati, et al (2001) Mol Biochem Parasitol 113:35 and GenBank numbers L29168, X62163 and AJ130942). Therefore, cysteine proteases also represent a potential chemotherapeutic target against *Leishmania* infections.

(b) Treatment of Disorders associated with Mammalian Cysteine Proteases

In certain embodiments, methods of treating disorders associated with mammalian cysteine proteases are also provided.

In one embodiment, the compounds of the invention may be used to treat a cancer associated with the activity of a mammalian cysteine protease. For example, cathepsin L, cathepsin B and cathepsin H are associated with increased invasiveness, malignancy and growth status of numerous cancers including breast carcinoma, oral squamous cell carcinoma, melanoma, transitional cell carcinoma of the bladder, intestinal adenoma, colorectal carcinoma, neuroblastoma and prostate carcinoma (see, for example, Kawasaki, et al, Oral Surg Oral Med Oral Pathol Oral Radiol Endod (2002) 93:446; Staack, et al, Urology (2002) 59:308; Levicar, et al, Cancer Detect Prev (2002) 26:42). Additionally, mRNA and protein expression of cathepsin K, a likely contributor to bone metastasis in breast cancer, has been observed in breast cancer cells (Ishikawa, et al, Mol Carcinog (2001) 32:84).

In other embodiment, the compounds of the invention may be used to treat an inflammatory disorder associated with aberrant activity of a mammalian cysteine protease. For example, the catalytic action of cathepsin B has been associated with rheumatoid arthritis, atherosclerotic plaque rupture and vascular inflammation, T cell migration in allergic lung inflammation, and as a contributing protease to multiple organ failure (see, Zwicky, et al, Biochem J (2002) 367:209-217; Chen, et al, Circulation (2002) 105:2766; Layton, et al, Inflamm Res (2001) 50:400; and Jochum, et al, Am J Respir Crit Care Med (1994) 150:S123). Additionally, chronic inflammation and extracellular matrix degradation preliminary to abdominal aortic aneurysm is associated with a 30-fold increased transcriptional expression of cathepsin H (Tung, et al, J Vasc Surg (2001) 34:143). Numerous studies have demonstrated the efficacy of inhibiting cathepsin L or cathepsin B in counteracting pathogenic processes of cancer and inflammation (see, for example, Katunuma, et al, Arch Biochem Biophys (2002) 397:305; Katunuma, et al, Adv Enzyme Regul (2002) 42:159; Greenspan, et al, J Med Chem (2001) 44:4524; Kobayashi, et al, Cancer Res (1992) 52:3610; Kolkhorst, V, et al, J Cancer Res Clin Oncol (1998) 124:598; Krueger, et al, Cancer Res (1999) 59:6010; Sexton and Cox, Melanoma Res (1997) 7:97; Cox, et al, Melanoma Res (1999) 9:369; Castino, et al, supra; and Layton, et al, supra).

Assays for Cysteine Protease Inhibition

In certain embodiments, the compounds of the invention may be screened for effectiveness against cathepsin-L like cysteine proteases in vitro and for effectiveness in disrupting the infectious life cycle of a parasite or malignancy potential of a cancer cell in cell culture and in vivo disease model systems.

For in vitro cysteine protease inhibition determinations, a compound's effectiveness can be given by an IC50 value. In these assays, the enzyme to be inhibited (e.g., a cruzain or cruzipain, a rhodesain, a brucipain, a congopain, a falcipain, CPB2.8 Delta CTE, a cathepsin-L, a cathepsin-B, a cathepsin-H, a cathepsin-K, a cathepsin-S) is first incubated with varying concentrations (about 20-50,000 nM) of a test compound. To this is added a short peptide substrate of the enzyme of 1 to 10 amino acids, usually a di- or tri-peptide substrate, which is labeled with either a fluorogenic or chromogenic moiety. An exemplary chromogenic moiety is p-nitro-anilide (pNA). Fluorogenic labels are generally comprised of a fluorescent donor, such as ortho-aminobenzoic acid (Abz) or benzyloxycarbonyl (Z), and a fluorescent quencher, such as 7-(4-methyl)-coumarylamide (AMC), methyl-7-aminocoumarin amide (MCA), 7-amino-4-trifluoromethylcoumarin (AFC) or N-(ethylenediamine)-2,4-dinitr-ophenyl amide (EDDnp), where the donor and quencher are on either terminus of the peptide substrate. Exemplary peptide substrates include Phe-Arg, Arg-Arg, Phe-Arg-X (X=Ala, Arg), and Phe-X-Ser-Arg-Gln (X=Arg, 4-aminomethyl-phenylalanine (Arm), 4-aminomethyl-N-isopropyl-phenylalanin-e (Iaf), 4-piperidinyl-alanine (Ppa) or 4-aminocyclohexyl-alanine (Aca)). Cleavage of the labeled substrate induces a chromogenic or fluorescent signal that is measured using spectrophotometer or a spectrofluorometer, respectively. Signals induced in the presence of varying concentrations of test compound are measured in comparison to a positive control of enzyme and substrate and a negative control of enzyme in diluent (e.g., DMSO). Spontaneous cleavage of substrate is measured in controls with substrate alone. IC50 values are determined graphically using compound inhibitor concentrations in the linear portion of a plot of inhibition versus log [I]. Inhibition of a target protease is achieved when the IC50 value is less than about 1000 nM, preferably less than about 500, 300 or 100 nM, more preferably less than about 90, 80, 70, 60, 50, 40, 30, 20 or 10 nM. In particularly preferred embodiments, inhibition of the target protease occurs at least than about 10, 9, 8, 7, 6, 5, 4, 3, 2, 1.5, 1.0, 0.5, 0.1, or 0.01 nM.

Anti-parasitic capacities of the compounds can be measured using cell culture assays. Cultured mammalian cells that are susceptible to infection by a target protozoan, such as for example, macrophages, erythrocytes, lymphocytes, fibroblasts or other cutaneous cells, hepatocytes, cardiocytes or myocytes are infected with infectious parasitic bodies, such as trypomastigotes to introduce trypanosome infection, merozoites to introduce *plasmodium* infection, or promastigotes to introduce *leishmania* infection. The culture medium is replaced to remove superfluous infectious parasitic bodies and to add test protease inhibitor compounds. Positive or treated control cultures are given a known parasitic inhibitor. For example, N-methyl piperazine-Phe-homoPhe-v-inyl sulfone phenyl (N-Pip-F-hF-VSPh) is known to inhibit trypanosomes. Negative or untreated control cultures are given only diluent (e.g., DMSO) in medium. Cultures are maintained for a time period that encompasses several intracellular cycles of the target parasite in untreated controls, usually about 30 days, but as long as 35, 40, 45 or 50 days or longer, as necessary. Cells are monitored, usually daily but this can be more or less often, for the presence or absence of parasitic infection, usually by contrast phase microscopy. The comparative effectiveness of each test protease inhibitor compound is determined from plots of the duration of the intracellular cycle of the target parasite in treated versus untreated control cultures (generally measured in days).

The ability of compounds of the present invention to inhibit cell invasiveness and migration can also be tested using cellular motility and cellular invasion assays. These assays are particularly applicable to measuring the inhibition of migration of cancer and inflammatory cells whose migration requires, at least in part, the catalytic activity of at least one cysteine protease such as a cathepsin-L, a cathepsin-B, a cathepsin-H, a cathepsin-K or a cathepsin-S. In vitro cellular motility assays are generally carried out using transwell chambers (available from Corning-Costar), with upper and lower culture compartments separated by filters, for example, polycarbonate filters with 8 .mu.m pore size. In vitro cellular invasion assays are conducted using matrigel precoated filters (for example, 100 µg/cm matrigel on a filter with 8 µm pore size; available from Becton Dickinson). Prior to invasion assays, the matrigel matrix is reconstituted with serum-free cell culture medium. Excess media is removed from the filters and a chemoattractant is placed in the lower compartment of a transwell chamber, for example 5 µg/ml collagen I can be used for a tumor cell. A specified number of cells radiolabeled with $^3$H-thymidine are seeded onto the filter in motility assays or onto the reconstituted matrigel basement membrane for invasion assays. Cells passing through the filters and attaching to the lower sides of uncoated or matrigel-coated are harvested using trypsin/EDTA, and cell-bound radioactivity is measured in a liquid scintillation counter. The number of migrating cells is calculated by measuring the radioactivity of cells on the underside of a filter in comparison to the radioactivity of a parallel culture containing an identical number of cells to what was originally seeded on the top of the filter or matrigel coating.

The ability of the protease inhibitor compounds to prevent or treat parasitic infections or cancer cell or inflammatory cell invasion or migration in a host subject also can be tested using in vivo disease models. Experimental animal disease models for trypanosomiasis, *leishmania*, and malaria are known in the art. For example, murine models for trypanosomiasis are disclosed in Duthie and Kahn, J Immunol (2002) 168:5778, Mucci, et al, Proc Natl Acad Sci (2002) 99:3896, Zuniga, et al, J Immunol (2002) 168:3965 and in Guarner, et al (2001) Am J Trop Med Hyg 65:152. Murine models for *leishmania* are described in Rhee, et al, J Exp Med (2002) 195:1565, and in Hommel, et al, Ann Trop Med Parasitol (1995) 89 Supp 1:55. Murine models of malaria are published in Sanni, et al, Methods Mol Med (2002) 72:57, Renia, et al, Methods Mol Med (2002) 72:41, and Li, et al, Med Microbiol Immunol (2001) 189:115. In mouse parasitic disease models, for example, infected mice are administered a test compound of the present invention, and then monitered for amelioration or abatement of infection in comparison to infected, but untreated control mice. Alternatively, uninfected mice are treated with a test compound and then inoculated with a infectious parasitic body to determine the capacity of the compound to prevent parasitic infection. Disease models for cancer and inflammation are also well documented in the published literature. Murine disease models for human cancers require immunodeficient mice (reviewed in Bankert, et al, Front Biosci (2002) 7:c44 and in Hann and Balmain, Curr Opin Cell Biol (2001) 13:778). Additional animal cancer models are discussed in Bast, et al, Cancer Medicine, $5^{th}$ Ed., B. C. Decker, Hamilton, Ontario, Canada).

Administration and Pharmaceutical Compositions

Pharmaceutically and physiologically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., Remington's Pharmaceutical Sciences, 17th ed., 1989). Suitable methods of administration include oral, nasal, rectal, and parenteral administration. Other delivery methods known to those of skill in the art can be used, e.g., liposomes, microspheres, and the like. The compounds of the invention can also be forumulated as prodrugs for ease of delivery.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of pain, the compounds utilized in the pharmaceutical method of the invention are administered at a therapeutically or prophylacticlaly effective dose, e.g., the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds of the invention can be administered in combination with other therapeutic compounds, either in the same pharmaceutical preparation, or in separate pharmaceutical preparations. The additional therapeutic or prophylactic compounds may be used to treat the same disease as the compound of the invention, e.g., a parasitic disease, a protozoan disease, or a cancer, or can be used to treat a second disease other than the disease treated by the compound of the invention. One or more compounds of the invention can be administered in the same pharmaceutical composition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

Kits

The present invention also provides kits for use by a consumer for treating disease. The kits comprise a) a pharmaceutical composition comprising a compound of the invention and a pharmaceutically acceptable carrier, vehicle or diluent; and, optionally, b) instructions describing a method of using the pharmaceutical composition for treating the specific disease. The instructions may also indicate that the kit is for treating disease while substantially reducing the concomitant liability of adverse effects associated with estrogen administration.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

EXAMPLES

The following examples are provided by way of illustration only and not by way of limitation. Those of skill in the art will readily recognize a variety of noncritical parameters that could be changed or modified to yield essentially similar results.

Compound Synthesis

General Section

Chemicals were obtained from commercial companies such as Acros Chemicals, Aldrich Chemical Company, Alfa Aesar, Lancaster Chemicals, and Fisher Scientific. Reactions which involved air or moisture sensitive reagents were performed in oven-dried glassware under nitrogen atmosphere using dried syringes, needles and cannulas to transfer solvents and reagents. Reactions were monitoring by silica gel thin layer chromatography (TLC) using Merk Kieselgel 60 $F_{254}$ glass backed plates. The plates were visualized by the use of a multiband 254/365 nm UV lamp, iodine or by dipping either in a solution of vanillin (in ethanolic sulphuric acid), PMA (in ethanol), anisaldehyde (in ethanol), ceric sulfate (in sulfuric acid), DNP (in an aqueous ethanolic sulfuric acid) or potassium permanganate (in basic water) followed by heating. Gas chromatography (Hewlett Packard 5890 Series II with a SE-54 column) and/or gas chromatography mass spectrometry (Hewlett Packard GCD system with electron impact ionization) were also used to monitor reactions. Flash chromatography was carried out with silica gel (230-400 mesh) purchased from BODMAN industries. Solvents used for chromatography and workups ($CH_2Cl_2$, hexanes, THF and acetone) were purified by distillation prior to use. Ethyl acetate, methanol, ethanol, diethyl ether and other solvents were purchased from the above mentioned companies as anhydrous solvents and use without further purification. Evaporation or removal of the solvents were performed with a rotary evaporator in vacuo followed by a further drying of the compound with a mechanical pump at vacuum pressures of <0.5 Torr.

Structure elucidation of the products was carried out using spectroscopic techniques such as NMR, IR and MS. $^1$H NMR spectra were recorded at 300 or 360 MHz on a Bruker DPX-300 and AMX-360 spectrometers. $^{13}$C spectra were recorded at 75 or 90 MHz and $^{31}$P spectra were recorded at 121 MHz. All NMRs were recorded in $CDCl_3$ (0.03% of TMS) unless stated otherwise. Chemical shifts, which are expressed in ppm ($\delta$), are referenced to tetramethylsilane (TMS). The NMR patterns are reported as singlets (s), doublets (d), triplets (t), quartets (q), multiplets (m), etc and the coupling constants (J) are reported in Hz. All the spectra are reported in a decoupled mode unless stated otherwise. Special NMR techniques such as low and high temperature NMR and NOESY were carried out on the Bruker AMX-360 spectrometer. Homonuclear decoupling, resolution enhancement, 2D NMR was performed on both spectrometers. NMR processing data was carried out using WinNMR, Mestrec or Nuts. IR spectra were run either neat (for liquids and solutions) or as nujol mulls (for solids) on a Genesis II FTIR spectrometer. The melting points, which were recorded uncorrected, were determined on a Thomas Hoover capillary melting point apparatus.

Example I

Synthesis of Propiophenone Derivatives

3-Bromopropiophenone thiosemicarbazone (5). (Du, X.; Guo, C.; Hansell, E.; Doyle, P. S.; Caffrey, C. R.; Holler, T. P.; McKerrow, J. H.; Cohen, F. E. J. Med. Chem. 2002, 45, 2695-2707) Into a round bottom flask containing 3-bromopropiophenone (0.508 g, 2.34 mmol), 20 mL of anhydrous methanol were added and the solution was refluxed for 15 minutes. To the warm ketone solution, thiosemicarbazide (0.184 g, 2.04 mmol) and 1% solution of HOAc (0.2 mL) were added. The reaction mixture was refluxed under nitrogen atmosphere for 17 h, at which point, the solvent was evaporated and, the crude reaction mixture was purified by flash chromatography (30% EtOAc/70% hex) to obtain 0.2498 g (0.873 mmol) of the product in a 37% yield.

$^1$H NMR (300 MHz, methyl sulfoxide-$d_6$, $\delta$): 10.39 (s, NH, 1H), 8.35 (br s, $NH_2$, 1H), 8.17 (t, J=1.7, ArH, 1H), 8.12 (br s, $NH_2$, 1H), 7.87 (ddd, J=7.9, 1.6, 0.8, ArH, 1H), 7.57 (ddd, J=7.9, 1.9, 0.8, ArH, 1H), 7.34 (t, J=7.9, ArH, 1H), 2.86 (q, J=7.4, $CH_2$, 2H), 0.99 (t, J=7.5, $CH_3$, 3H).

$^{13}$C NMR (75 MHz, methyl sulfoxide-$d_6$): $\delta$ 179.0, 150.3, 138.8, 131.9, 130.5, 129.0, 125.8, 122.2, 19.1, 10.8.

Dept 135 NMR (75 MHz, methyl sulfoxide-$d_6$): $\delta$ 132.3 (CH), 130.9 (CH), 129.5 (CH), 126.3 (CH), 19.6 ($CH_2$), 11.3 ($CH_3$).

3-Nitropropiophenone thiosemicarbazone (6). Into a round bottom flask containing 3-nitropropiophenone (1.02 g, 5.53 mmol), 30 mL of anhydrous methanol were added and the solution was refluxed for about 15 minutes. To the warm ketone solution, thiosemicarbazide (0.485 g, 5.33 mmol) and 1% solution of HOAc (0.4 mL) were added. The reaction mixture was refluxed under nitrogen atmosphere for 30 h, at which point, the solvent was evaporated and, the crude reaction mixture was purified by flash chromatography (50% EtOAc/50% hex) to obtain 0.8119 g (3.22 mmol) of the product in a 58% yield.

$^1$H NMR (300 MHz, acetone-$d_6$, $\delta$): 9.62 (br s, NH, 1H), 8.66 (t, J=1.9, ArH, 1H), 8.38 (ddd, J=7.9, 1.8, 1.0, ArH, 1H), 8.25 (ddd, J=8.2, 2.3, 1.0, ArH, 1H), 8.07 (br s, $NH_2$, 1H), 7.72 (t, J=8.1, ArH, 1H), 7.66 (br s, $NH_2$, 1H), 3.09 (q, J=7.7, $CH_2$, 2H), 1.23 (t, J=7.7, $CH_3$, 3H).

3-Aminopropiophenone thiosemicarbazone (8). Into a round bottom flask containing 3-nitropropiophenone (0.102 g, 0.406 mmol), Zn (0.884 g, 13.5 mmol) and $CaCl_2$ (0.0398 g, 0.271 mmol), 7.5 mL of EtOH—$H_2O$ (4:1 ratio) were added and the solution was refluxed for about 1.5 h. At the end of this time, the reaction mixture was filtered through celite and silica gel, rinsed twice with EtOH (2×5 mL) and the solvent evaporated. The product was purified by flash chromatography (40% EtOAc/60% hex) to obtain 0.0420 g (0.189 mmol) of the amine in a 47% yield.

E-isomer: $^1$H NMR (300 MHz, acetone-d$_6$, δ): 9.39 (br s, NH, 1H), 7.79 (br s, NH$_2$, 1H), 7.54 (br s, NH$_2$, 1H), 7.24 (m, ArH, 1H), 7.09 (m, ArH, 2H), 6.72 (m, ArH, 1H), 4.70 (br s, NH, 2H), 2.89 (q, J=7.6, CH$_2$, 2H), 1.16 (t, J=7.4, CH$_3$, 3H).

Dept 135 NMR (75 MHz, acetone-d$_6$): δ 129.0 (CH), 115.5 (CH), 115.2 (CH), 112.3 (CH), 19.6 (CH$_2$), 10.5 (CH$_3$).

3-(t-Butyldimethylsilyloxy)benzaldehyde. Into a round bottom flask containing 3-hydroxybenzaldehyde (0.658 g, 5.23 mmol) and DMAP (0.0646 g, 0.52 mmol), first 10 mL of anhydrous CH$_2$Cl$_2$ and then 0.89 mL of NEt$_3$ (0.634 g, 6.27 mmol) were added. After the reaction mixture was stirred under nitrogen at 0° C. for 10 minutes, 5 mL of a CH$_2$Cl$_2$ solution of TBSCl (0.976 g, 6.28 mmol) were added. The reaction mixture was stirred for 2.5 h at room temperature and, then it was filtered through silica gel-florisil, rinsed with CH$_2$Cl$_2$ and the organic phase dried under Na$_2$SO$_4$. After evaporating the solvent, 1.1308 g (4.79 mmol) of pure product was obtained in a 92% yield.

$^1$H NMR (300 MHz, CDCl$_3$): δ 9.94 (s, CHO, 1H), 7.46 (td, J=7.5, 1.3, ArH, 1H), 7.39 (t, J=7.7, ArH, 1H), 7.31 (dd, J=2.5, 1.5, 1.0, ArH, 1H), 7.09 (ddd, J=7.9, 2.5, 1.2, ArH, 1H), 0.98 (s, C(CH$_3$)$_3$, 9H), 0.21 (s, Si(CH$_3$)$_2$, 6H).

3-(t-Butyldimethylsilyloxyphenyl)-1-propanol. 9 mL of anhydrous Et$_2$O were poured into a dry flask containing Mg (0.442 g, 18.0 mmol) and few crystals of I$_2$. While the reaction mixture was being stirred at room temperature under nitrogen, 10 drops of ethyl bromide (1.86 g, 17.1 mmol) were added. After the reaction mixture became cloudy (approximately 10 minutes after bromide addition), the rest of the ethyl bromide (1.3 mL) was added during a 50-minute period and the reaction mixture was refluxed at 45° C. for 2 h. When almost all the Mg was consumed, the reaction flask was put in ice bath and 5 mL of an ethereal solution of the appropriate aldehyde (1.85 g, 7.82 mmol) were added during 15 minutes. The reaction mixture was stirred for 4 h at room temperature, at which point, first H$_2$O was added and, then 3 mL of HCl (6M). The product was extracted twice from the aqueous phase with Et$_2$O and the resultant organic phase was washed once with H$_2$O and once with brine. After drying the organic phase under Na$_2$SO$_4$, the solvent was evaporated and 1.9952 g (7.50 mmol) of pure product was obtained in a 91% yield.

$^1$H NMR (300 MHz, CDCl$_3$, δ):7.18 (t, J=7.8, ArH, 1H), 6.91 (ddd, J=7.5, 2.6, 0.6, ArH, 1H), 6.82 (dd, J=2.3, 1.8, ArH, 1H), 6.74 (ddd, J=8.0, 2.5, 1.0, ArH, 1H), 4.53 (t, J=6.6, CHOH, 1H), 1.83 (br s, OH, 1H), 1.75 (m, CH$_2$, 2H), 0.97 (s, C(CH$_3$)$_3$, 9H), 0.90 (dd, J=8.6, 6.3, CH$_3$, 3H), 0.18 (s, Si(CH$_3$)$_2$, 6H).

1-(3-t-Butyldimethylsilyloxyphenyl)propan-1-one. 30 mL of anhydrous CH$_2$Cl$_2$ were poured into a flask containing PCC (2.63 g, 12.0 mmol) and celite (2.6 g). The suspension was stirred at 0° C. under nitrogen for 10 minutes, at which point, 12 mL of a CH$_2$Cl$_2$ solution of the appropriate alcohol (2.00 g, 7.50 mmol) were added. After the reaction was stirred at room temperature for 4 h, 20 mL of Et$_2$O were added and the reaction mixture was filtered through fluorisil-silica gel and rinsed with extra Et$_2$O (10 mL). The organic phase was dried under Na$_2$SO$_4$ and the solvent was evaporated to afford 1.842 g (6.98 mmol) of pure product in an 86% yield.

$^1$H NMR (300 MHz, CDCl$_3$, δ):7.54 (ddd, J=7.7, 1.6, 1.0, ArH, 1H), 7.41 (dd, J=2.5, 1.6, ArH, 1H), 7.30 (t, J=7.9, ArH, 1H), 7.01 (ddd, J=8.0, 2.5, 1.0, ArH, 1H), 2.96 (q, J=7.2, CH$_2$, 2H), 1.20 (t, J=7.2, CH$_3$, 3H), 0.98 (s, C(CH$_3$)$_3$, 9H), 0.20 (s, Si(CH$_3$)$_2$, 6H).

$^{13}$C NMR (75 MHz, CDCl$_3$): δ 200.6, 156.0, 138.4, 129.5, 124.7, 121.1, 119.3, 31.9, 25.7, 18.2, 8.3, −4.4

Dept 135 NMR (75 MHz, CDCl$_3$): δ 129.5 (CH), 124.7 (CH), 121.11 (CH), 119.3 (CH), 31.9 (CH$_2$), 25.7 (CH$_3$), 8.3 (CH$_3$), −4.4 (CH$_3$).

1-(3-t-Butyldimethylsilyloxyphenyl)propan-1-one thiosemicarbazone. Into a round bottom flask containing the appropriate TBS protected ketone (0.645 g, 2.44 mmol), 20 mL of anhydrous methanol were added and the solution was refluxed for about 15 minutes. To the warm ketone solution, thiosemicarbazide (0.214 g, 2.85 mmol) and 1% solution of HOAc (0.5 mL) were added. The reaction mixture was refluxed under nitrogen atmosphere for 23 h, at which point, the solvent was evaporated and, the crude reaction mixture was purified by flash chromatography (20% EtOAc/80% hex) to obtain 0.6741 g (2.07 mmol) of a mixture of E/Z thiosemicarbazones (1.2:1 ratio) in an 85% yield.

E-isomer: $^1$H NMR (300 MHz, CDCl$_3$, δ): 8.80 (br s, NH, 1H), 7.35 (t, J=7.9, ArH, 1H), 7.34 (br s, NH$_2$, 1H), 7.15 (dd, J=1.6, 0.6, ArH, 1H), 6.91 (ddd, J=8.3, 2.4, 0.9, ArH, 1H), 6.90 (dt, J=7.2, 2.2, ArH, 1H), 6.42 (br s, NH$_2$, 1H), 2.70 (q, J=7.8, CH$_2$, 2H), 1.21 (t, J=7.7, CH$_3$, 3H), 1.00 (s, C(CH$_3$)$_3$, 9H), 0.22 (s, Si(CH$_3$)$_2$, 6H).

$^{13}$C NMR (75 MHz, CDCl$_3$): δ 179.4, 156.0, 152.7, 137.6, 129.6, 121.6, 119.4, 118.1, 25.7, 20.4, 18.2, 10.6, −4.3.

Dept 135 NMR (75 MHz, CDCl$_3$): δ 129.6 (CH), 121.7 (CH), 119.5 (CH), 118.1 (CH), 25.7 (CH), 20.4 (CH$_2$), 10.7 (CH$_3$), −4.3 (CH$_3$).

Z-isomer: $^1$H NMR (300 MHz, CDCl$_3$, δ): 8.62 (br s, NH, 1H), 7.29 (br s, NH$_2$, 1H), 7.26 (t, J=7.7, ArH, 1H), 6.79 (ddd, J=7.5, 1.4, 1.1, ArH, 1H), 6.66 (dd, J=2.2, 1.9, ArH, 1H), 6.29 (br s, NH$_2$, 1H), 2.56 (q, J=7.4, CH$_2$, 2H), 1.11 (t, J=7.4, CH$_3$, 3H), 1.00 (s, C(CH$_3$)$_3$, 9H), 0.24 (s, Si(CH$_3$)$_2$, 6H).

$^{13}$C NMR (75 MHz, CDCl$_3$): δ 178.9, 156.8, 155.4, 134.2, 131.0, 121.6, 119.4, 118.4, 31.5, 25.6, 18.2, 10.6, −4.3.

Dept 135 NMR (75 MHz, CDCl$_3$): δ 131.0 (CH), 121.7 (CH), 119.4 (CH), 118.4 (CH), 31.5 (CH$_2$), 25.7 (CH$_3$), 10.7 (CH$_3$), −4.3 (CH$_3$).

1-(3-Hydroxyphenyl)-1-propanone thiosemicarbazone (7). At 0° C. and under nitrogen, the appropriate TBS protected thiosemicarbazone (0.344 g, 1.06 mmol) was dissolved with 10 mL of anhydrous CH$_2$Cl$_2$. To the well stirred solution, 1.6 mL of a solution (1M in THF) of TBAF (0.418 g, 1.6 mmol) was added and the reaction mixture was stirred at room temperature for 1.5 h. At the end of this period of time, H$_2$O was added to the reaction mixture, the product was extracted once from the aqueous phase with CH$_2$Cl$_2$ and the resultant organic phase was washed once with H$_2$O, once with brine and dried under Na$_2$SO$_4$. The product was purified from the crude of reaction by flash chromatography (30% EtOAc/70% hex) to afford 0.2338 g (1.05 mmol) of thiosemicarbazone in a 99% yield.

E-isomer: $^1$H NMR (360 MHz, CDCl$_3$, δ): 9.38 (br s, NH, 1H), 7.72 (br s, NH$_2$, 1H), 7.47 (br s, NH$_2$, 1H), 7.34 (m, ArH, 1H), 7.26 (m, ArH, 2H), 6.96 (m, ArH, 1H), 2.80 (q, J=7.6, CH$_2$, 2H), 1.20 (t, J=7.5, CH$_3$, 3H).

Dept 135 NMR (90 MHz, CDCl$_3$): δ 134.7 (CH), 123.3 (CH), 122.1 (CH), 118.6 (CH), 25.4 (CH$_2$), 15.9 (CH$_3$).

1-Phenyl-1-(3-bromophenyl)methanol. 6 mL of anhydrous Et$_2$O were poured into a dry flask containing Mg (0.448 g, 18.2 mmol) and few crystals of I$_2$. While the reaction mixture was stirred at room temperature under nitrogen, 14 drops of bromobenzene (2.74 g, 17.5 mmol) were added. After the reaction mixture became cloudy (approximately 5 minutes after bromide addition), the rest of the bromobenzene (1.86 mL) was added during a 30-minute period and, the reaction mixture was refluxed at 40° C. for 2.5 h. When almost all the Mg was consumed, the reaction flask was put in ice bath and 3 mL of an ethereal solution of m-bromobenzaldehyde (1.50 g, 7.93 mmol) were added during 10 minutes. The reaction mixture was stirred for 2 h at room temperature, at which point, first H$_2$O was added and, then 6.6 mL of HCl (6M). The product was extracted twice from the aqueous phase with Et$_2$O and the resultant organic phase was washed once with H$_2$O and once with brine. After drying the organic phase under Na$_2$SO$_4$, the solvent was evaporated and the product was purified by flash chromatography (10% EtOAc/90% hex). 1.8611 g (7.08 mmol) of pure alcohol was obtained in a 89% yield.

$^1$H NMR (300 MHz, CDCl$_3$, δ): 7.56 (t, J=1.8, ArH, 1H), 7.34 (m, ArH, 7H), 7.19 (t, J=7.8, ArH, H), 5.79 (s, CHOH, 1H), 2.23 (br s, OH, 1H).

Dept 135 NMR (75 MHz, CDCl$_3$): δ 130.6 (CH), 130.1 (CH), 129.5 (CH), 128.7 (CH), 128.0 (CH), 126.6 (CH), 125.1 (CH), 75.7 (CHOH).

EIMS: m/z (% rel. intensity) 264 (M$^+$+2, 16), 262 (M$^+$, 16), 185 (23), 183 (28), 105 (100), 77 (40).

Example II

Synthesis of Benzophenone Thiosemicarbazones Derivatives

Phenyl(3-bromophenyl) ketone. 30 mL of anhydrous CH$_2$Cl$_2$ were poured into a flask containing PCC (2.34 g, 10.6 mmol) and celite (2.3 g). The suspension was stirred at 0° C. under nitrogen for 10 minutes, at which point, 10 mL of a CH$_2$Cl$_2$ solution of the appropriate alcohol (1.86 g, 7.08 mmol) were added. After the reaction was stirred at room temperature for 4 h, 15 mL of Et$_2$O were added and the reaction mixture was filtered through Fluorisil-silica gel bed and rinsed with extra Et$_2$O (10 mL). The organic phase was dried under Na$_2$SO$_4$ and the solvent was evaporated to afford 1.7852 g (6.84 mmol) of pure product in a 97% yield.

$^1$H NMR (300 MHz, CDCl$_3$, δ): 7.93 (t, J=1.8, ArH, 1H), 7.78 (m, ArH, 2H), 7.71 (dd, J=8.1, 1.6, ArH, 2H), 7.61 (tt, J=7.4, 1.3, ArH, 1H), 7.49 (tt, J=6.8, 1.5, ArH, 2H), 7.36 (t, J=7.8, ArH, 1H).

Dept 45 NMR (75 MHz, CDCl$_3$): δ 135.3 (CH), 132.9 (CH), 132.8 (CH), 130.1 (CH), 129.9 (CH), 128.6 (CH), 128.5 (CH).

EIMS: m/z (% rel. intensity) 262 (M$^+$+2, 25), 260 (M$^+$, 25), 185 (16), 183 (16), 105(100), 77 (33).

Phenyl(3-bromophenyl) ketone thiosemicarbazone (13) Into a round bottom flask containing the appropriate ketone (1.79 g, 6.84 mmol), 30 mL of anhydrous methanol were added and the solution was refluxed for about 15 minutes. To the warm ketone solution, thiosemicarbazide (0.600 g, 6.59 mmol) and 1% solution of HOAc (0.8 mL) were added. The reaction mixture was refluxed under nitrogen atmosphere for 26 h, at which point, the solvent was evaporated and, the crude reaction mixture was purified by flash chromatography (30% EtOAc/70% hex) to obtain 0.7739 g (2.32 mmol) of the product in a 34% yield.

E-isomer: $^1$H NMR (300 MHz, methyl sulfoxide-d$_6$, δ): 8.69 (br s, NH, 1H), 8.57 (br s, NH$_2$, 1H), 8.42 (br s, NH$_2$, 1H), 8.07 (s, ArH, 1H), 7.59 (m, ArH, 4H), 7.36 (m, ArH, 4H).

1,1-Bis(3-bromophenyl)methanol. 7 mL of anhydrous Et$_2$O were poured into a dry flask containing Mg (0.530 g, 21.6 mmol) and few crystals of I$_2$. While the reaction mixture was being stirred at room temperature under nitrogen, 6 drops of m-dibromobenzene (4.92 g, 20.9 mmol) were added. After the reaction mixture became cloudy (approximately 30 minutes after bromide addition), the rest of the dibromobenzene (2.6 mL) was added during a 30-minute period and, the reaction mixture was refluxed at 30° C. for 1.5 h. When almost all the Mg was consumed, the reaction flask was put in ice bath and, 5 mL of an ethereal solution of m-bromobenzaldehyde (1.77 g, 9.38 mmol) were added during 10 minutes. The reaction mixture was stirred for 3.5 h at room temperature, at which point, first H$_2$O (4 mL) was added and, then 5 mL of HCl (6M). The product was extracted twice from the aqueous phase with Et$_2$O and the resultant organic phase was washed once with H$_2$O and once with brine. After drying the organic phase under Na$_2$SO$_4$, the solvent was evaporated and the product was purified by flash chromatography (10% EtOAc/90% hex). 1.99 g (5.82 mmol) of pure alcohol was obtained in a 62% yield.

$^1$H NMR (360 MHz, CDCl$_3$, δ): 7.53 (t, J=1.8, ArH, 2H), 7.41 (ddd, J=7.7, 2.0, 1.4, ArH, 2H), 7.27 (dtd, J=7.5, 1.6, 0.4, ArH, 2H), 7.21 (t, J=7.7, ArH, 2H), 5.75 (s, CHOH, 1H), 2.31 (br s, OH, 1H).

Dept 135 NMR (90 MHz, CDCl$_3$): δ 131.0 (CH), 130.3 (CH), 129.6 (CH), 125.2 (CH), 75.0 (CHOH).

EIMS: m/z (% rel. intensity) 344 (M$^+$+4, 8), 342 (M$^+$+2, 17), 340 (M$^+$, 8), 185 (100), 183(89), 157 (25), 77 (50).

Bis(3-bromophenyl) ketone. 30 mL of anhydrous CH$_2$Cl$_2$ were poured into a flask containing PCC (1.92 g, 8.73 mmol) and celite (1.9 g). The suspension was stirred at 0° C. under nitrogen for 10 minutes, at which point, 10 mL of a CH$_2$Cl$_2$ solution of the appropriate alcohol (1.99 g, 5.82 mmol) were added. After the reaction was stirred at room temperature for 5.5 h, 15 mL of Et$_2$O were added and the reaction mixture was filtered through fluorisil-silica gel and rinsed with extra Et$_2$O (10 mL). The organic phase was dried under Na$_2$SO$_4$ and the solvent was evaporated to afford 1.673 g (4.92 mmol) of pure product in a 85% yield.

$^1$H NMR (300 MHz, CDCl$_3$, δ): 7.92 (t, J=1.8, ArH, 2H), 7.73 (ddd, J=8.0, 2.0, 1.1, ArH, 2H), 7.68 (ddd, J=7.7, 1.6, 1.2, ArH, 2H), 7.37 (t, J=7.8, ArH, 2H).

$^{13}$C NMR (75 MHz, CDCl$_3$): δ 193.7, 138.8, 135.7, 132.7, 130.0, 128.5, 122.8.

Bis(3-bromophenyl) ketone thiosemicarbazone (14) Into a round bottom flask containing the appropriate ketone (1.044 g, 3.07 mmol), 35 mL of anhydrous methanol were added and the solution was refluxed for about 15 minutes. To the warm ketone solution, thiosemicarbazide (0.294 g, 3.23 mmol) and 1% solution of HOAc (1.5 mL) were added. The reaction mixture was refluxed under nitrogen atmosphere for 46 h, at which point, the solvent was evaporated and, the crude reaction mixture was purified by flash chromatography (20% EtOAc/80% hex) to obtain 0.231 g (0.559 mmol) of the product in an 18% yield.

$^1$H NMR (360 MHz, CDCl$_3$, δ): 8.59 (br s, NH, 1H), 7.72 (s, ArH, 2H), 7.41 (m, ArH, 6H), 6.92 (br s, NH$_2$, 1H).

Example III

Synthesis of Tetrahydronaphthalene Derivatives

5-Bromo-1-tetralone. (Cornelius, L. A. H.; Combs, D. W. Synthetic Communications 1994, 24(19), 2777-2788) Into a round bottom flask kept at 0° C., AlCl$_3$ (19.6 g, 146.8 mmol) was added and the reaction system was put under nitrogen. 8 mL of tetralone (8.62 g, 58.9 mmol) were added during a 10-minute period, at which point, the reaction mixture was heated in an oil bath at 90° C. for about 45 minutes before adding 3.6 mL of Br$_2$ (11.2 g, 70.1 mmol). The reaction mixture was stirred at 90° C. for an hour before 30 mL of ice-water and 20 mL of NaHCO$_3$ were added. The product was extracted twice from the aqueous phase with Et$_2$O and, the resultant organic phase was washed once with NaHCO$_3$, once with brine and dried under Na$_2$SO$_4$. The crude reaction mixture was purified by flash chromatography (2.5% EtOAc/97.5% hex) which afforded 5.87 g (26.1 mmol) of the product in a 44% yield.

$^1$H NMR (300 MHz, CDCl$_3$, δ): 8.01 (dd, J=7.8, 1.3, ArH, 1H), 7.73 (dd, J=7.9, 1.3, ArH, 1H), 7.18 (tt, J=7.9, 0.6, ArH, 1H), 3.01 (t, J=6.2, CH$_2$, 2H), 2.64 (dd, J=6.7, 5.6, CH$_2$, 2H), 2.15 (td, J=13.0, 6.5, CH$_2$, 2H).

$^{13}$C NMR (75 MHz, CDCl$_3$): δ 197.5, 143.4, 137.3, 134.9, 127.7, 126.5, 124.8, 38.2, 30.0, 22.3.

Dept 135 NMR (75 MHz, CDCl$_3$): δ 137.3 (CH), 127.7 (CH), 126.5 (CH), 38.2 (CH$_2$), 30.0 (CH$_2$), 22.3 (CH$_2$).

EIMS: m/z (% rel. intensity) 226 (M$^+$+2, 93), 224 (M$^+$, 93), 211 (25), 209 (25), 198 (100), 196 (100), 170 (50), 168 (50), 145 (25), 115 (45), 89 (60), 63 (28).

7-Bromo-1-tetralone. (Cornelius, L. A. H.; Combs, D. W. Synthetic Communications 1994, 24(19), 2777-2788) Into a round bottom flask kept at 0° C., AlCl$_3$ (19.6 g, 146.8 mmol) was added and the reaction system was put under nitrogen. 8 mL of tetralone (8.62 g, 58.9 mmol) were added during a 10-minute period, at which point, the reaction mixture was heated in an oil bath at 90° C. for about 45 minutes before adding 3.6 mL of Br$_2$ (11.2 g, 70.1 mmol). The reaction mixture was stirred at 90° C. for an hour before 30 mL of ice-water and 20 mL of NaHCO$_3$ were added. The product was extracted twice from the aqueous phase with Et$_2$O and, the resultant organic phase was washed once with NaHCO$_3$, once with brine and dried under Na$_2$SO$_4$. The crude reaction mixture was purified by flash chromatography (2.5% EtOAc/97.5% hex) which afforded 5.36 g (23.8 mmol) of the product in a 40% yield.

$^1$H NMR (300 MHz, CDCl$_3$, δ): 8.14 (d, J=2.2, ArH, 1H), 7.56 (dd, J=8.1, 2.2, ArH, 1H), 7.13 (d, J=8.2, ArH, 1H), 2.90 (t, J=6.1, CH$_2$, 2H), 2.64 (dd, J=5.7, 5.5, CH$_2$, 2H), 2.12 (td, J=12.7, 6.4, CH$_2$, 2H).

Dept 135 NMR (75 MHz, CDCl$_3$): δ 136.1 (CH), 130.7 (CH), 130.0 (CH), 38.8 (CH$_2$), 29.2 (CH$_2$), 23.1 (CH$_2$).

EIMS: m/z (% rel. intensity) 226 (M$^+$+2, 100), 224 (M$^+$, 100), 211 (25), 209 (25), 198 (75), 196 (75), 170 (60), 168 (60), 145 (25), 115 (45), 89 (58), 63 (28).

5-Bromo-1-tetralone thiosemicarbazone (20) Into a round bottom flask containing the appropriate ketone (0.343 g, 1.52 mmol), 16 mL of anhydrous methanol were added and the solution was refluxed for about 15 minutes. To the warm ketone solution, thiosemicarbazide (0.182 g, 2.00 mmol) and about 80 mg of TsOH were added. The reaction mixture was refluxed under nitrogen atmosphere for 7.5 h, at which point, the white solid formed was filtered and, rinsed with cold MeOH. After drying the solid under reduced pressure, 0.3577 g (1.20 mmol) of the product was obtained in a 79% yield.

$^1$H NMR (300 MHz, acetone-d$_6$, δ): 9.25 (s, NH, 1H), 8.22 (dd, J=8.0, 1.2, ArH, 1H), 7.87 (br s, NH$_2$, 1H), 7.55 (dd, J=7.9, 1.2, ArH, 1H), 7.47 (br s, NH$_2$, 1H), 7.10 (tt, J=7.9, 0.6, ArH, 1H), 2.88 (t, J=6.2, CH$_2$, 2H), 2.79 (t, J=6.5, CH$_2$, 2H), 1.99 (tt, J=6.6, 1.1, CH2, 2H).

Dept 135 NMR (75 MHz, acetone-d$_6$): δ 133.1 (CH), 127.4 (CH), 124.4 (CH), 29.5 (CH$_2$), 24.7 (CH$_2$), 21.0 (CH$_2$).

7-Bromo-1-tetralone thiosemicarbazone (21) Into a round bottom flask containing the appropriate ketone (0.347 g, 1.54 mmol), 10 mL of anhydrous methanol were added and the solution was refluxed for about 10 minutes. To the warm ketone solution, thiosemicarbazide (0.246 g, 2.70 mmol) and 0.7 mL of 1% solution of HOAc were added. The reaction mixture was refluxed under nitrogen atmosphere for 18 h, at which point, the solvent was evaporated. The crude reaction mixture was purified by flash chromatography (30% EtOAc/70% hex) which afforded 0.314 g (1.05 mmol) of the product in a 68% yield.

$^1$H NMR (300 MHz, acetone-d$_6$, δ): 9.31 (br s, NH, 1H), 8.38 (d, J=2.1, ArH, 1H), 8.15 (br s, NH$_2$, 1H), 7.57 (br s, NH$_2$, 1H), 7.43 (dd, J=8.2, 2.2, ArH, 1H), 7.16 (d, J=8.2, ArH, 1H), 2.82 (t, J=6.6, CH$_2$, 2H), 2.79 (t, J=6.5, CH$_2$, 2H), 1.96 (m, CH$_2$, 2H).

Dept 135 NMR (75 MHz, acetone-d$_6$): δ 131.8 (CH), 130.6 (CH), 127.3 (CH), 28.6 (CH$_2$), 25.0 (CH$_2$), 21.2 (CH$_2$).

7-Bromo-2-tetralone. Into a round bottom flask kept at 0° C., AlCl$_3$ (3.93 g, 29.5 mmol) and 5 mL of CH$_2$Cl$_2$ were added. The reaction system was put under nitrogen and stirred for about 7 minutes before adding 20 mL of a CH$_2$Cl$_2$ solution of β-tetralone (2.16 g, 14.7 mmol). After the reaction mixture was stirred for almost 10 minutes, 10 mL of Br$_2$ (2.58 g, 16.2 mmol) were added and, the reaction mixture was stirred at room temperature for an hour. At the end of this period of time, the reaction mixture was poured into 50 mL of ice-water and, the product was extracted 3 times from the aqueous phase with EtOAc. The resultant organic phase was washed once with brine and dried under Na$_2$SO$_4$. After the crude reaction mixture was purified by flash chromatography (5% EtOAc/95% hex), 2.364 g (10.5 mmol) of monobromide was obtained in a 71% yield.

$^1$H NMR (300 MHz, CDCl$_3$, δ): 7.33 (dd, J=8.1, 2.0, ArH, 1H), 7.27 (d, J=2.0, ArH, 1H), 7.10 (d, J=8.0, ArH, 1H), 3.55 (s, CH$_2$, 2H), 3.02 (t, J=6.6, CH$_2$, 2H), 2.53 (t, J=6.7, 6.4, CH$_2$, 2H).

$^{13}$C NMR (75 MHz, CDCl$_3$): δ 209.2, 135.6, 135.5, 130.9, 129.8, 129.2, 120.4, 44.5, 37.8, 27.8.

Dept 135 NMR (75 MHz, CDCl$_3$): δ 131.0 (CH), 129.9 (CH), 129.3 (CH), 44.6 (CH$_2$), 37.9 (CH$_2$), 27.9 (CH$_2$).

5,7-Dibromo-2-tetralone and 6,8-dibromo-2-tetralone. Into a round bottom flask kept at 0° C., AlCl$_3$ (2.26 g, 16.9 mmol) was added and the reaction system was put under nitrogen. 1 mL of β-tetralone (1.08 g, 7.37 mmol) were added during a 10-minute period, at which point, the reaction mixture was heated in an oil bath at 90° C. for about 30 minutes before adding 0.45 mL of Br$_2$ (1.41 g, 8.82 mmol). The reaction mixture was stirred at 85° C. for an hour before 15 mL of ice-water and 8 mL of NaHCO$_3$ were added. The product was extracted twice from the aqueous phase with Et$_2$O and, the resultant organic phase was washed once with NaHCO$_3$, once with brine and dried under Na$_2$SO$_4$. The crude reaction mixture was purified by flash chromatography (10% EtOAc/90% hex) which afforded 2 major compounds. 0.110 g (0.362 mmol) of 6,8-dibromo-2-tetralone (less polar compound) was obtained in a 6% yield.

$^1$H NMR (300 MHz, CDCl$_3$, δ): 7.34 (s, ArH, 2H), 3.66 (s, CH$_2$, 2H), 3.24 (t, J=6.8, CH$_2$, 2H), 2.60 (t, J=6.9, CH$_2$, 2H).

$^{13}$C NMR (75 MHz, CDCl$_3$): δ 207.8, 137.9, 135.1, 131.93, 131.90, 123.2, 122.9, 44.6, 37.9, 29.4.

Dept 135 NMR (75 MHz, CDCl$_3$): δ 131.99 (CH), 131.95 (CH), 44.7 (CH$_2$), 38.0 (CH$_2$), 29.5 (CH$_2$).

The more polar compound was recrystallized (MeOH-hex) to yield 0.2602 g (0.856 mmol) of 5,7-dibromo-2-tetralone in a 10% yield.

$^1$H NMR (300 MHz, CDCl$_3$, δ): 7.64 (d, J=1.8, ArH, 1H), 7.34 (d, J=1.8, ArH, 1H), 3.58 (s, CH$_2$, 2H), 3.06 (t, J=6.5, CH$_2$, 2H), 2.57 (t, J=6.7, CH$_2$, 2H).

$^{13}$C NMR (75 MHz, CDCl$_3$): δ 207.9, 140.1, 133.3, 133.2, 130.4, 124.7, 120.6, 44.1, 38.1, 29.0.

Dept 135 NMR (75 MHz, CDCl$_3$): δ 133.2 (CH), 130.1 (CH), 44.1 (CH$_2$), 38.1 (CH$_2$), 29.0 (CH$_2$).

7-Bromo-2-tetralone thiosemicarbazone (69) Into a round bottom flask containing the appropriate ketone (0.358 g, 1.59 mmol), 10 mL of anhydrous methanol were added and the solution was refluxed for about 15 minutes. To the warm ketone solution, thiosemicarbazide (0.269 g, 2.96 mmol) and about 50 mg of TsOH were added. The reaction mixture was refluxed under nitrogen atmosphere for 16.5 h, at which point, the solid formed was filtered and recrystallized with MeOH. After drying the solid under reduced pressure, 0.333 g (1.12 mmol) of the product was obtained in a 70% yield.

$^1$H NMR (300 MHz, acetone-$d_6$, δ): 9.25 (s, N$\underline{H}$, 1H), 8.22 (dd, J=8.0, 1.2, ArH, 1H), 1-Tetralone p-toluensulfonhydrazone. Into a round bottom flask containing 1-tetralone (4.40 g, 30.1 mmol), 30 mL of anhydrous methanol were added and the solution was refluxed for about 15 minutes. To the warm ketone solution, p-toluensulfonhydrazide (8.49 g, 44.2 mmol) and about 57 mg of TsOH were added. The reaction mixture was refluxed under nitrogen atmosphere for 4.5 h, at which point, the solid formed was filtered and recrystallized with MeOH. After drying the solid under reduced pressure, 8.064 g (25.7 mmol) of the product was obtained in an 87% yield.

$^1$H NMR (300 MHz, CDCl$_3$, δ): 7.95 (dd, J=7.6, 1.5, ArH, 1H), 7.94 (d, J=8.4, ArH, 2H), 7.85 (br s, NH, 1H), 7.32 (d$\underline{d}$, J=8.6, 0.5, ArH, 2H), 7.$\underline{21}$ (m, ArH, 2H), 7.0$\underline{8}$ (dd, J=7.0, 1.8, ArH, 1H), 2.$\overline{70}$ (t, J=6.0, C$\underline{H_2}$, 2$\underline{H}$), 2.47 (t, J=6.6, C$\underline{H_2}$, 2H), 2.4$\overline{1}$ (s, CH$_3$, 3H), 1.88 (p, $\overline{J}$=6.4, C$\underline{H_2}$, 2H).

Dept 135 NMR (75 MHz, CDCl$_3$): δ 129.61 (CH), 129.57 (CH), 128.3 (CH), 128.2 (CH), 126.5 (CH), 125.$\overline{0}$ (CH), 29.3 ($\overline{C}H_2$), 25.5 ($\overline{C}H_2$), 21.6 ($\overline{C}H_3$), 21.4 ($\overline{C}H_2$).

1-[1-(3,4-Dihydronaphthalenyl)]-1-ethanol. Into a dry round bottom flask containing 1-tetralone p-toluenensulfonhydrazone (0.957 g, 3.05 mmol), 20 mL of TMEDA were added and, nitrogen was circulated through the reaction system. After the solution was cooled at −50° C., 4.9 mL of BuLi (2.5 M/hex, 12.3 mmol) were added and, the reaction mixture was stirred first at −50° C. for 30 minutes and then at room temperature for another 30 minutes. After bubbling stopped, the flask was cooled at 0° C. and, 1 mL of acetaldehyde (0.786 g, 17.9 mmol) was added. The reaction was stirred at 0° C. for 2 h, at which point, 10 mL of ice water were added. The product was extracted once from the aqueous phase with EtOAc and, the combined organic phase was washed 3 times with H$_2$O and with brine. The organic phase was dried under Na$_2$SO$_4$ and, the solvent was removed under vacuum. After the product was purified by flash chromatography (20% EtOAc/80% hex), 0.155 g (0.891 mmol) was obtained in a 29% yield.

$^1$H NMR (300 MHz, CDCl$_3$, δ): 7.38 (d, J=7.3, ArH, 1H), 7.18 (m, ArH, 3H), 6.17 (td, J=4.6, 1.0, C=CH, 1H), $\overline{4}$.89 (q, J=6.3, CH$\overline{O}$H, 1H), 2.72 (t, J=8.0, C$\underline{H_2}$, 2H), $\overline{2}$.27 (m, C$\underline{H_2}$, 2H), 1.7$\overline{6}$ (br s, OH, 1H), 1.45 (d, J=$\overline{6}$.4, CH$_3$, 3H).

$^{13}$C NMR (75 M$\overline{H}$z, CDCl$_3$): δ 140.4, 13$\overline{6}$.9, 133.3, 127.8, 126.9, 126.4, 123.8, 122.9, 67.4, 28.3, 22.8, 22.6.

Dept 135 NMR (75 MHz, CDCl$_3$): δ 127.8 (CH), 126.9 (CH), 126.4 (CH), 123.8 (CH), 122.9 (CH), 67.4 ($\overline{C}H$), 28.2 ($\overline{C}H_2$), 22.8 ($\overline{C}H_3$), 22.6 ($\overline{C}H_2$).

[1-(3,4-Dihydronaphthalenyl)]methyl ketone (37) Into a round bottom flask containing 15 mL of a 15% w/w solution of Dess-Martin reagent (3.07 g, 7.24 mmol), 10 mL of a CH$_2$Cl$_2$ solution of the appropriate alcohol (0.470 g, 2.70 mmol) were added and, the reaction mixture was stirred under nitrogen for 2 h at room temperature. The crude reaction mixture was poured into 75 mL of a mixture of NaHCO$_3$—Na$_2$S$_2$O$_3$ (2:1 ratio) and stirred for 10 minutes. The product was extracted twice from the aqueous phase with Et$_2$O and, the resultant organic phase was washed once with H$_2$O, once with brine and dried under Na$_2$SO$_4$. The ethereal solution was filtered through silica gel and concentrated under vacuum to afford 0.460 g (2.67 mmol) of the product in a 99% yield.

$^1$H NMR (300 MHz, CDCl$_3$, δ): 7.69 (dd, J=8.7, 2.2, ArH, 1H), 7.19 (m, ArH, 3H), 7.01 (t, J=4.9, C=CH, 1H), 2.74 $\overline{(t}$, J=7.4, C$\underline{H_2}$, 2H), $\overline{2}$.46 (s, CH$_3$, 3H), 2.42 (m, $\overline{C}H_2$, 2H).

$^{13}$C N$\overline{MR}$ (75 MHz, CD$\overline{Cl_3}$): δ 199.4, 139.2, $\overline{13}$6.4, 130.9, 130.8, 127.7, 127.6, 126.6, 126.5, 27.8, 27.5, 23.7.

Dept 135 NMR (75 MHz, CDCl$_3$): δ 139.2 (CH), 127.7 (CH), 127.6 (CH), 126.6 (CH), 126.5 (CH), 27.9 ($\overline{C}H_3$), 27.5 ($\overline{C}H_2$), 23.8 ($\overline{C}H_2$).

5,7-Dibromo-2-tetralone thiosemicarbazone (41) Into a round bottom flask containing ketone 37 (0.0783 g, 0.455 mmol), 10 mL of anhydrous methanol were added and the solution was refluxed for about 15 minutes before adding thiosemicarbazide (0.0683 g, 0.856 mmol) and 13 mg of TsOH. The reaction mixture was refluxed under nitrogen atmosphere for 15 h. The crude reaction mixture was purified by column chromatography (40% EtOAc/60% hex) which afforded 0.028 g (0.114 mmol) of the product (65% trans isomer and 35% cis) in a 25% yield.

Trans isomer: $^1$H NMR (300 MHz, CDCl$_3$, δ): 8.62 (br s, N H, 1H), 7.26 (br s, NH$_2$, 1H), 7.17 (m, ArH, 3H), 6.76 (d, $\overline{J}$=7.1, ArH, 1H), 6.27 $\overline{(br}$ s, NH$_2$, 1H), 6.02 ($\overline{t, J}$=4.5, C=CH, 1H), 2.85 (t, J=8.1, C$\underline{H_2}$, 2H), $\overline{2}$.34 (m, C$\underline{H_2}$, 2H), 2.15 (s, $\overline{C}$ H$_3$, 3H).

Dept 135 NMR (75 MHz, CDCl$_3$): δ 129.6 (CH), 128.7 (CH), 128.5 (CH), 127.2 (CH), 123.6 ($\underline{C}H$), 27.2 ($\overline{C}H_2$), 24.2 ($\overline{C}H_3$), 22.7 ($\overline{C}H_2$).

Cis isomer: $^1$H NMR (300 MHz, CDCl$_3$, δ): 8.67 (br s, NH, 1H), 7.26 (br s, NH$_2$, 1H), 7.17 (m, ArH, 4H), 6.31 (t, J=$\overline{4.8}$, C=CH, 1H), 6.2$\overline{7}$ (br s, NH$_2$, 1H), 2.$\overline{76}$ (t, J=7.6, C$\underline{H_2}$, 2H), 2.46 ($\overline{m}$, C$\underline{H_2}$, 2H), 2.13 (s, $\overline{C}H_3$, 3H).

Dept 135 NMR (75 MHz, $\overline{C}$DCl$_3$): δ 130.9 (CH), 127.9 (CH), 127.6 (CH), 126.4 (CH), 125.3 (CH), 27.9 ($\overline{C}H_2$), 23.3 ($\overline{C}H_2$). 15.6 ($\overline{C}H_3$).

7-Bromo-1-tetralone p-toluensulfonhydrazone. Into a round bottom flask containing the appropriate tetralone (2.20 g, 9.78 mmol), 40 mL of anhydrous methanol were added and the solution was refluxed for about 15 minutes. To the warm ketone solution, p-toluenesulfonhydrazide (2.82 g, 14.7 mmol) and about 20 mg of TsOH were added. The reaction mixture was refluxed under nitrogen atmosphere for 7 h, at which point, the solid formed was filtered and recrystallized with MeOH. After drying the solid under reduced pressure, 3.44 g (8.75 mmol) of the product was obtained in a 90% yield.

$^1$H NMR (360 MHz, methanol-$d_6$, δ): 8.00 (d, J=2.1, ArH, 1H), 7.86 (d, J=8.3, ArH, 2H), 7.67 (br s, NH, 1H), 7.35 $\overline{(d}$, J=8.2, ArH, 2H), 7.31 (d$\overline{d}$, J=8.2, 2.1 ArH, 1$\overline{H})$, 6.98 (d, J=8.2, ArH, 1H$\overline{)}$, $\overline{2}$.66 (t, J=5.8, C$\underline{H_2}$, 2H), 2.4$\overline{9}$ (t, J=6.6, C$\underline{H_2}$, 2H), 2.4$\overline{0}$ (s, CH$_3$, 3H), 1.83 (p, $\overline{J}$=6.1, C$\underline{H_2}$, 2H).

$^{13}$C NMR (75 MHz, methanol-$d_6$): δ 152.7, 145.0, 139.6, 136.9, 134.8, 132.8, 131.0, 130.3, 128.8, 128.4, 120.8, 29.6, 26.4, 22.2, 21.7.

Dept 135 NMR (75 MHz, methanol-$d_6$): δ 132.8 (CH), 131.0 (CH), 130.3 (CH), 128.8 (CH), 128.4 (CH), $\overline{29}$.6 ($\overline{C}H_2$), $\overline{2}$6.4 ($\overline{C}H_2$), 2$\overline{2.2}$ ($\overline{C}H_2$), 21.$\overline{7}$ (CH$_3$).

1-(7-Bromo-3,4-dihydronaphthalen-$\overline{1}$-yl)-2-propen-1-ol. Into a dry round bottom flask containing the appropriate hydrazone (3.44 g, 8.76 mmol), 30 mL of TMEDA were added and, nitrogen was circulated through the reaction system. After the solution was cooled at −50° C., 14 mL of BuLi (2.5 M/hex, 35 mmol) were added and, the reaction mixture was stirred first at −50° C. for 40 minutes and then at room temperature for another 40 minutes. After bubbling stopped, the flask was cooled at 0° C. and, 2.4 mL of acrolein (1.96 g, 34.9 mmol) were added. The reaction was stirred at 0° C. for 3 h, at which point, 30 mL of ice water were added. The product was extracted once from the aqueous phase with EtOAc and, the combined organic phase was washed 3 times with H$_2$O and with brine. The organic phase was dried under Na$_2$SO$_4$ and, the solvent was removed under vacuum. After the product was purified by flash chromatography (10% EtOAc/90% hex), 0.246 g (0.928 mmol) was obtained in an 11% yield.

$^1$H NMR (300 MHz, CDCl$_3$, δ): 7.60 (d, J=2.0, ArH, 1H), 7.26 (dd, J=8.0, 2.0, ArH, 1H), 7.00 (d, J=8.0, ArH, 1H), 6.22 (td, J=4.6, 0.7, C=CH, 1H), 6.05 (ddd, J=17.3, 10.5, 5.4, CH=CH$_2$, 1H), 5.40 (dt, J=17.3, 1.5, C=CH$_2$, 1H), 5.25 (dt, J=10.4, 1.4, C=CH$_2$, 1H), 5.10 (dd, J=5.3, 1.0, CHOH, 1H), 2.67 (t, J=8.0, CH$_2$, 2H), 2.30 (m, CH$_2$, 2H), 1.92 (br s, OH, 1H).

Dept 135 NMR (75 MHz, CDCl$_3$): δ 138.9 (CH), 129.6 (CH), 129.2 (CH), 128.2 (CH), 126.7 (CH), 116.1 (CH$_2$), 72.6 (CHOH), 27.5 (CH$_2$), 22.8 (CH$_2$).

1-(7-Bromo-3,4-dihydronaphthalen-1-yl)propenone (38) Into a round bottom flask containing 2.4 mL of a 15% w/w solution of Dess-Martin reagent (0.471 g, 1.11 mmol), 10 mL of a CH$_2$Cl$_2$ solution of the appropriate alcohol (0.123 g, 0.463 mmol) were added and, the reaction mixture was stirred under nitrogen for 1 h at room temperature. The crude reaction mixture was poured into 50 mL of a mixture of NaHCO$_3$—Na$_2$S$_2$O$_3$ (1:1 ratio) and stirred for 10 minutes. The product was extracted twice from the aqueous phase with Et$_2$O and, the resultant organic phase was washed once with H$_2$O, once with brine and dried under Na$_2$SO$_4$. After the crude reaction mixture was purified by flash chromatography (5% EtOAc/95% hex), 0.0683 g (0.260 mmol) of the product was obtained in a 67% yield.

$^1$H NMR (300 MHz, CDCl$_3$, δ): 7.68 (d, J=2.0, ArH, 1H), 7.30 (dd, J=8.0, 2.1, ArH, 1H), 7.03 (d, J=8.0, ArH, 1H), 6.85 (t, J=4.8, C=CH, 1H), 6.77 (dd, J=17.2, 10.5, CH=CH$_2$, 1H), 6.32 (dd, J=17.2, 1.5, C=CH$_2$, 1H), 5.90 (dd, J=10.5, 1.5, C=CH$_2$, 1H), 2.73 (t, J=7.9, CH$_2$, 2H), 2.45 (td, J=8.0, 4.9, CH$_2$, 2H).

$^{13}$C NMR (75 MHz, CDCl$_3$): δ 192.6, 139.0, 137.7, 135.0, 134.7, 132.9, 130.6, 130.2, 129.1, 128.9, 120.2, 26.9, 23.3.

Dept 135 NMR (75 MHz, CDCl$_3$): δ 138.9 (CH), 134.7 (CH), 130.6 (CH), 130.2 (CH$_2$), 129.2 (CH), 128.9 (CH), 26.9 (CH$_2$), 23.3 (CH$_2$).

Dept 90 NMR (75 MHz, CDCl$_3$): δ 138.9 (CH), 134.6 (CH), 130.6 (CH), 129.1 (CH), 128.8 (CH).

1-(3,4-Dihydronaphthalen-1-yl)prop-2-en-1-ol. Into a dry round bottom flask containing the appropriate hydrazone (1.995 g, 6.35 mmol), 20 mL of TMEDA were added and, nitrogen was circulated through the reaction system. After the solution was cooled at −50° C., 10.2 mL of BuLi (2.5 M/hex, 25.5 mmol) were added and, the reaction mixture was stirred first at −50° C. for 40 minutes and then at room temperature for 35 minutes. After bubbling stopped, the flask was cooled at 0° C. and, 2.0 mL of acrolein (1.63 g, 29.1 mmol) were added. The reaction was stirred at 0° C. for 5 h, at which point, 30 mL of ice water were added. The product was extracted once from the aqueous phase with EtOAc and, the combined organic phase was washed 3 times with H$_2$O and with brine. The organic phase was dried under Na$_2$SO$_4$ and, the solvent was removed under vacuum. After the product was purified by flash chromatography (10% EtOAc/90% hex), 0.1165 g (0.626 mmol) was obtained in a 10% yield.

$^1$H NMR (300 MHz, CDCl$_3$, δ): 7.46 (d, J=6.7, ArH, 1H), 7.18 (m, ArH, 3H), 6.19 (td, J=4.6, 0.9, C=CH, 1H), 6.12 (ddd, J=17.2, 10.4, 5.3, CH=CH$_2$, 1H), 5.42 (dt, J=17.2, 1.5, C=CH$_2$, 1H), 5.24 (dt, J=10.4, 1.5, C=CH$_2$, 1H), 5.18 (d, J=3.9, CHOH, 1H), 2.75 (t, J=8.0, CH$_2$, 2H), 2.31 (dddd, J=6.3, 4.7, 3.2, 0.9, CH$_2$, 2H), 1.95 (br s, OH, 1H).

$^{13}$C NMR (75 MHz, CDCl$_3$): δ 139.3, 137.8, 136.7, 133.0, 127.7, 126.9, 126.6, 126.3, 123.4, 115.6, 72.6, 28.1, 22.9.

Dept 135 NMR (75 MHz, CDCl$_3$): δ 139.4 (CH), 127.8 (CH), 127.0 (CH), 126.7 (CH), 126.3 (CH), 123.5 (CH), 115.7 (CH$_2$), 72.7 (CHOH), 28.1 (CH$_2$), 23.0 (CH$_2$).

1-(3,4-Dihydronaphthalen-1-yl)propenone. Into a round bottom flask containing 2.6 mL of a 15% w/w solution of Dess-Martin reagent (0.532 g, 1.26 mmol), 9 mL of a CH$_2$Cl$_2$ solution of the appropriate alcohol (0.117 g, 0.626 mmol) were added and, the reaction mixture was stirred under nitrogen for 2 h at room temperature. The crude reaction mixture was poured into 75 mL of a mixture of NaHCO$_3$—Na$_2$S$_2$O$_3$ (2:1 ratio) and stirred for 10 minutes. The product was extracted twice from the aqueous phase with Et$_2$O and, the resultant organic phase was washed once with H$_2$O, once with brine and dried under Na$_2$SO$_4$. After the crude reaction mixture was purified by flash chromatography (10% EtOAc/90% hex), 0.0825 g (0.448 mmol) of the product was obtained in a 72% yield.

$^1$H NMR (300 MHz, CDCl$_3$, δ): 7.46 (d, J=8.7, ArH, 1H), 7.18 (m, ArH, 3H), 6.77 (dd, J=17.3, 10.5, CH=CH$_2$, 1H), 6.77 (t, J=4.8, C=CH, 1H), 6.32 (dd, J=17.3, 1.6, C=CH$_2$, 1H), 5.87 (dd, J=10.5, 1.6, C=CH$_2$, 1H), 2.79 (t, J=7.9, CH$_2$, 2H), 2.45 (ddd, J=8.7, 7.2, 4.9, CH$_2$, 2H).

$^{13}$C NMR (75 MHz, CDCl$_3$): δ 193.4, 138.8, 137.4, 136.1, 135.1, 131.1, 129.7, 127.8, 127.6, 126.5, 125.9, 27.4, 23.4.

Dept 135 NMR (75 MHz, CDCl$_3$): δ 137.4 (CH), 135.2 (CH), 129.8 (CH$_2$), 127.8 (CH), 127.7 (CH), 126.6 (CH), 125.9 (CH), 27.5 (CH$_2$), 23.4 (CH$_2$).

5-Bromo-1-tetralone p-toluenesulfonhydrazone. Into a round bottom flask containing the appropriate tetralone (2.28 g, 10.1 mmol), 40 mL of anhydrous methanol were added and the solution was refluxed for about 15 minutes. To the warm ketone solution, p-toluensulfonhydrazide (2.92 g, 15.2 mmol) and 20 mg of TsOH were added. The reaction mixture was refluxed under nitrogen atmosphere for 7 h, at which point, the solid formed was filtered and recrystallized with MeOH. After drying the solid under reduced pressure, 3.494 g (8.89 mmol) of the product was obtained in an 88% yield.

$^1$H NMR (360 MHz, methanol-d$_6$, δ): 7.90 (dd, J=8.0, 1.2, ArH, 1H), 7.85 (d, J=8.4, ArH, 2H), 7.54 (s, NH, 1H), 7.47 (dd, J=7.9, 1.2, ArH, 1H), 7.30 (dd, J=8.6, 0.6, ArH, 2H), 7.02 (t, J=7.9, ArH, 1H), 2.78 (t, J=6.2, CH$_2$, 2H), 2.48 (t, J=6.6, CH$_2$, 2H), 2.38 (s, CH$_3$, 3H), 1.85 (p, J=6.5, CH$_2$, 2H).

$^{13}$C NMR (75 MHz, methanol-d$_6$): δ 153.2, 144.6, 139.4, 136.5, 134.9, 133.9, 130.1, 128.6, 127.9, 125.0, 124.9, 30.0, 25.8, 21.7.

Dept 135 NMR (75 MHz, methanol-d$_6$): δ 133.9 (CH), 130.07 (CH), 128.6 (CH), 127.9 (CH), 124.9 (CH), 29.9 (CH$_2$), 25.8 (CH$_2$), 21.73 (CH$_3$), 21.69 (CH$_2$).

1-(5-Bromo-3,4-dihydronaphthalen-1-yl)-2-propen-1-ol. Into a dry round bottom flask containing the appropriate hydrazone (3.49 g, 8.89 mmol), 30 mL of TMEDA were added and, nitrogen was circulated through the reaction system. After the solution was cooled at −50° C., 14.2 mL of BuLi (2.5 M/hex, 35 mmol) were added and, the reaction mixture was stirred first at −50° C. for 40 minutes and then at room temperature for another 40 minutes. After bubbling stopped, the flask was cooled at 0° C. and, 2.4 mL of acrolein (1.96 g, 34.9 mmol) were added. The reaction was stirred at 0° C. for 4 h, at which point, 30 mL of ice water were added. The product was extracted once from the aqueous phase with EtOAc and, the combined organic phase was washed 3 times with H$_2$O and with brine. The organic phase was dried under Na$_2$SO$_4$ and, the solvent was removed under vacuum. After the product was purified by flash chromatography (10% EtOAc/90% hex), 0.319 g (1.20 mmol) was obtained in a 14% yield.

$^1$H NMR (300 MHz, CDCl$_3$, δ): 7.42 (dd, J=8.8, 1.0, ArH, 1H), 7.39 (dd, J=9.3, 1.2, ArH, 1H), 7.03 (t, J=7.9, ArH, 1H), 6.21 (td, J=4.7, 0.8, C=CH, 1H), 6.04 (ddd, J=17.2, 10.4, 5.3, CH=CH$_2$, 1H), 5.39 (dt, J=17.3, 1.5, C=CH$_2$, 1H), 5.23 (dt, J=10.4, 1.4, C=CH$_2$, 1H), 5.13 (dd, J=5.3, 1.0, CHOH, 1H), 2.88 (t, J=8.1, CH$_2$, 2H), 2.32 (m, CH$_2$, 2H), 1.94 (br s, OH, 1H).

$^{13}$C NMR (90 MHz, CDCl$_3$): δ 139.0, 137.4, 136.0, 135.2, 131.2, 127.7, 127.3, 124.0, 122.8, 115.9, 77.6, 27.3, 22.5.

Dept 135 NMR (90 MHz, CDCl$_3$): δ 139.1 (CH), 131.3 (CH), 127.8 (CH), 127.4 (CH), 122.9 (CH), 116.0 (CH$_2$), 72.7 (CHOH), 27.6 (CH$_2$), 22.6 (CH$_2$).

1-(5-Bromo-3,4-dihydronaphthalen-1-yl)propenone. Into a round bottom flask containing 5 mL of a 15% w/w solution of Dess-Martin reagent (1.02 g, 2.41 mmol), 10 mL of a CH$_2$Cl$_2$ solution of the appropriate alcohol (0.319 g, 1.21 mmol) were added and, the reaction mixture was stirred under nitrogen for 1.5 h at room temperature. The crude reaction mixture was poured into 50 mL of a mixture of NaHCO$_3$—Na$_2$S$_2$O$_3$ (1:1 ratio) and stirred for 10 minutes. The product was extracted twice from the aqueous phase with Et$_2$O and, the resultant organic phase was washed once with H$_2$O, once with brine and dried under Na$_2$SO$_4$. After the crude reaction mixture was purified by flash chromatography (10% EtOAc/90% hex), 0.146 g (0.555 mmol) of the product was obtained in a 46% yield.

$^1$H NMR (300 MHz, CDCl$_3$, δ): 7.43 (dd, J=8.0, 1.1, ArH, 1H), 7.39 (d, J=7.7, ArH, 1H), 7.05 (t, J=7.9, ArH, 1H), 6.78 (t, J=4.8, C=CH, 1H), 6.73 (dd, J=17.3, 10.5, CH=CH$_2$, 1H), 6.30 (dd, J=17.3, 1.5, C=CH$_2$, 1H), 5.88 (dd, J=10.5, 1.5, C=CH$_2$, 1H), 2.93 (t, J=8.0, CH$_2$, 2H), 2.46 (td, J=8.0, 4.8, CH$_2$, 2H).

$^{13}$C NMR (75 MHz, CDCl$_3$): δ 192.9, 138.4, 137.8, 135.5, 135.0, 133.1, 132.0, 130.2, 127.5, 125.2, 123.7, 26.7, 23.0.

Dept 135 NMR (75 MHz, CDCl$_3$): δ 137.9 (CH), 135.1 (CH), 132.1 (CH), 130.2 (CH$_2$), 127.6 (CH), 125.3 (CH), 26.8 (CH$_2$), 23.1 (CH$_2$).

1,1-Dioxo-1-thiochroman-4-one. Into a round bottom flask containing thiochroman-4-one (0.804 g, 4.75 mmol), 6 mL of glacial HOAc and, 2.3 mL of a 35% w/w solution of H$_2$O$_2$ (0.914 g, 26.9 mmol) were added and, the solution was heated at 100° C. for 1 h. After the reaction mixture was cooled at room temperature, 10 mL of H$_2$O were added and the product was extracted twice with CH$_2$Cl$_2$ from the aqueous layer. The resultant organic phase was washed once with brine and dried under Na$_2$SO$_4$. After the solvent was removed, a solid was formed which was purified by recrystallization with EtOH. After drying the solid under reduced pressure, 0.649 g (3.31 mmol) of the product was obtained in a 70% yield.

$^1$H NMR (300 MHz, acetone-d$_6$, δ): 8.07 (ddd, J=7.7, 1.3, 0.6, ArH, 1H), 7.99 (ddd, J=7.8, 2.2, 0.7, ArH, 1H), 7.95 (td, J=7.8, 1.5, ArH, 1H), 7.86 (ddd, J=7.7, 6.7, 2.1, ArH, 1H), 3.94 (t, J=6.3, CH$_2$, 2H), 3.37 (t, J=6.3, CH$_2$, 2H).

$^{13}$C NMR (75 MHz, acetone-d$_6$): δ 191.3, 142.9, 135.6, 134.1, 131.6, 129.1, 124.0, 49.6, 37.5.

Dept 45 NMR (75 MHz, acetone-d$_6$): δ 134.8 (CH), 133.2 (CH), 128.2 (CH), 123.1 (CH), 48.8 (CH$_2$), 36.7 (CH$_2$).

5,7-Dibromo-2-tetralone thiosemicarbazone (70) Into a round bottom flask containing the appropriate ketone (0.379 g, 1.93 mmol), 15 mL of anhydrous methanol were added and the solution was refluxed for about 15 minutes before adding thiosemicarbazide (0.160 g, 1.76 mmol) and 4 mg of TsOH. After the reaction mixture was refluxed under nitrogen atmosphere for 5 h, a solid was formed which was filtered and further rinsed with MeOH. After the solid was dried under vacuum, 0.361 g (1.34 mmol) of the product was obtained in a 70% yield.

$^1$H NMR (300 MHz, methyl sulfoxide-d$_6$, δ): 10.62 (s, NH, 1H), 8.56 (dd, J=8.2, 2.1, ArH, 1H), 8.55 (br s, NH$_2$, 1H), 8.25 (br s, NH$_2$, 1H), 7.84 (m, ArH, 1H), 7.65 (m, ArH, 2H), 3.69 (t, J=6.3, CH$_2$, 2H), 3.30 (t, J=6.3, CH$_2$, 2H).

$^{13}$C NMR (75 MHz, Methyl Sulfoxide-d$_6$): δ 179.4, 139.8, 137.6, 132.7, 132.6, 129.9, 127.1, 122.4, 45.7, 24.4.

6-Bromothiochroman-4-one and 6,8-Dibromothiochroman-4-one. Into a round bottom flask kept at room temperature, AlCl$_3$ (1.81 g, 13.5 mmol) and, 1 mL of CH$_2$Cl$_2$ were added. The reaction system was put under nitrogen and stirred for about 7 minutes before adding 1 mL of a CH$_2$Cl$_2$ solution of thiochroman-4-one (1.11 g, 6.77 mmol). After the reaction mixture was stirred for almost 10 minutes, 2 mL of a CH$_2$Cl$_2$ solution of Br$_2$ (1.19 g, 7.44 mmol) were added and, the reaction mixture was stirred at room temperature for 16 h. At the end of this period of time, the reaction mixture was poured into 50 mL of ice-water and, the product was extracted 3 times from the aqueous phase with EtOAc. The resultant organic phase was washed once with brine and dried under Na$_2$SO$_4$. After the crude reaction mixture was purified by flash chromatography (15% EtOAc/85% hex), 0.648 g of a mixture of 6-monobromide (34% pure, 13% yield) and 6,8-dibromo (66% pure, 20% yield) was obtained.

6,8-Dibromo-thiocroman-4-one: $^1$H NMR (300 MHz, CDCl$_3$, δ): 8.18 (dd, J=2.2, 0.7, ArH, 1H), 7.77 (dd, J=2.2, 0.7, ArH, 1H), 3.22 (m, CH$_2$, 2H), 2.94 (m, CH$_2$, 2H).

$^{13}$C NMR (75 MHz, CDCl$_3$): δ 192.0, 142.5, 139.1, 136.0, 131.0, 122.2, 118.2, 37.8, 26.0.

6-Bromo-thiocroman-4-one: $^1$H NMR (300 MHz, CDCl$_3$, δ): 8.19 (dd, J=2.2, 0.4, ArH, 1H), 7.44 (ddd, J=8.5, 2.3, 0.6, ArH, 1H), 7.13 (dd, J=8.5, 0.3, ArH, 1H), 3.22 (m, CH$_2$, 2H), 2.93 (m, CH$_2$, 2H).

$^{13}$C NMR (75 MHz, CDCl$_3$): δ 192.7, 141.1, 133.3, 132.1, 131.8, 129.2, 118.7, 39.1, 26.5.

8-Bromothiochroman-4-one. Into a round bottom flask kept at 0° C., AlCl$_3$ (2.01 g, 15.1 mmol) and 9 mL of CH$_2$Cl$_2$ were added. The reaction system was put under nitrogen and stirred for about 7 minutes before adding 2 mL of a CH$_2$Cl$_2$ solution of thiochroman-4-one (1.24 g, 7.54 mmol). After the reaction mixture was stirred for almost 10 minutes, 4 mL of a CH$_2$Cl$_2$ solution of Br$_2$ (1.28 g, 7.98 mmol) were added during a 30-minute period and, the reaction mixture was stirred at 0° C. for 4 h. At the end of this period of time, the reaction mixture was poured into 50 mL of ice-water and, the product was extracted 3 times from the aqueous phase with EtOAc. The resultant organic phase was washed once with brine and dried under Na$_2$SO$_4$. After the crude reaction mixture was purified by flash chromatography (20% EtOAc/80% hex), 1.34 g of a mixture of 6-bromide (63% pure, 46% yield), 8-bromide (20% pure, 15% yield), and 6,8-dibromo (17% pure, 10% yield) was obtained.

8-Bromo-thiocroman-4-one: $^1$H NMR (300 MHz, CDCl$_3$, δ): 8.07 (ddd, J=7.9, 1.4, 0.7, ArH, 1H), 7.63 (ddd, J=7.7, 1.4, 0.7, ArH, 1H), 7.03 (td, J=7.9, 0.7, ArH, 1H), 3.22 (m, CH$_2$, 2H), 2.93 (m, CH$_2$, 2H).

6,8-Dibromo-1,1-dioxo-1-thiochroman-4-one. Into a round bottom flask containing 0.548 g of 6-bromothiochroman-4-one and 6,8-dibromothiochroman-4-one (0.361 g, 1.12 mmol of dibromo and 0.186 g, 0.766 mmol of monobromide), 6 mL of glacial HOAc and, 1 mL of a 35% w/w solution of H$_2$O$_2$ (0.400 g, 11.7 mmol) were added and, the solution was heated at 100° C. for 2 h. After the reaction mixture was cooled at room temperature, a solid was formed which was filtered and purified by recrystallized with EtOH-MeOH. After drying the solid under reduced pressure, 0.265 g (0.749 mmol) of the product was obtained in a 67% yield.

$^1$H NMR (300 MHz, CD$_2$Cl$_2$, δ): 8.22 (d, J=2.1, ArH, 1H), 8.16 (d, J=2.1, ArH, 1H), 3.75 (m, CH$_2$, 2H), 3.37 (m, CH$_2$, 2H).

$^{13}$C NMR (75 MHz, CD$_2$Cl$_2$): δ 188.8, 143.4, 139.5, 133.6, 131.6, 127.8, 119.4, 50.8, 36.6.

6-Bromo-1,1-dioxo-1-thiochroman-4-one. Into a round bottom flask containing 1.31 g of 8-bromothiochroman-4-one (0.824 g, 3.39 mmol of 6-bromo, 0.262 g, 1.08 mmol of 8-bromo and 0.222 g, 0.69 mmol of 6,8-dibromo-thiocroman-4-one), 15 mL of glacial HOAc and, 2.5 mL of a 35% w/w solution of H$_2$O$_2$ (0.993 g, 29.2 mmol) were added and, the solution was heated at 100° C. for 2 h. After the reaction mixture was cooled at room temperature, 10 mL of H$_2$O were added and the product was extracted twice with CH$_2$Cl$_2$ from the aqueous layer. The resultant organic phase was washed once with brine and dried under Na$_2$SO$_4$. After the solvent was removed, a solid was formed which was purified by recrystallized with EtOH—CH$_2$Cl$_2$. After drying the solid under reduced pressure, 0.653 g (1.76 mmol) of the product (74% pure) was obtained in a 52% yield.

$^1$H NMR (300 MHz, CD$_2$Cl$_2$, δ): 8.21 (d, J=2.0, ArH, 1H), 7.95 (dd, J=8.3, 2.0, ArH, 1H), 7.84 (d, J=8.3, ArH, 1H), 3.71 (m, CH$_2$, 2H), 3.38 (m, CH$_2$, 2H).

$^{13}$C NMR (75 MHz, CD$_2$Cl$_2$): δ 189.5, 143.4, 140.6, 138.1, 131.9, 128.6, 125.6, 49.6, 37.1.

6,8-Dibromo-1,1-dioxo-1-thiochroman-4-one thiosemicarbazone (24) Into a round bottom flask containing the appropriate thiochroman-4-one (0.218 g, 0.617 mmol), 15 mL of anhydrous methanol were added and the solution was refluxed for about 15 minutes before adding thiosemicarbazide (0.0512 g, 0.563 mmol) and 1.2 mg of TsOH. After the reaction mixture was refluxed under nitrogen atmosphere for 4 h, a solid was formed which was filtered and, then purified by recrystallzation with CH$_2$Cl$_2$-EtOH. After the solid was dried under vacuum, 0.115 g (0.269 mmol) of the product was obtained in a 44% yield.

$^1$H NMR (300 MHz, Methyl Sulfoxide-d$_6$, δ): 10.69 (s, NH, 1H), 8.82 (d, J=1.9, ArH, 1H), 8.59 (br s, NH$_2$, 1H), 8.53 (br s, NH$_2$, 1H), 8.11 (d, J=1.9, ArH, 1H), 3.76 (t, J=5.6, CH$_2$, 2H), 3.26 (t, J=5.6, CH$_2$, 2H).

$^{13}$C NMR (75 MHz, Methyl Sulfoxide-d$_6$): δ 179.4, 139.3, 137.6, 136.5, 135.7, 128.9, 126.4, 117.8, 47.4, 23.0.

6-Bromo-1,1-dioxo-1-thiochroman-4-one thiosemicarbazone (23) Into a round bottom flask containing 0.198 g of the appropriate thiochroman-4-one (0.147 g, 0.534 mmol), 10 mL of anhydrous methanol were added and the solution was refluxed for about 15 minutes before adding thiosemicarbazide (0.0598 g, 0.657 mmol) and 1.4 mg of TsOH. After the reaction mixture was refluxed under nitrogen atmosphere for 10 h, a solid was formed which was filtered and, then purified by column chromatography (30% EtOAc/70% hex). 0.0618 g (0.178 mmol) of the product was obtained in a 33% yield.

$^1$H NMR (300 MHz, Methyl Sulfoxide-d$_6$, δ): 10.59 (s, NH, 1H), 8.77 (d, J=1.8, ArH, 1H), 8.58 (br s, NH$_2$, 1H), 8.52 (br s, NH$_2$, 1H), 7.80 (dd, J=8.4, 1.9, ArH, 1H), 7.74 (d, J=8.4, ArH, 1H), 3.69 (t, J=6.3, CH$_2$, 2H), 3.27 (t, J=6.5, CH$_2$, 2H).

$^{13}$C NMR (75 MHz, Methyl Sulfoxide-d$_6$): δ 179.4, 138.8, 136.6, 134.5, 132.7, 129.1, 127.1, 124.6, 45.5, 24.5.

7-Bromo-4-chromanone. Into a round bottom flask kept at 0° C., AlCl$_3$ (0.533 g, 3.99 mmol) and, 5 mL of CH$_2$Cl$_2$ was added. The reaction system was put under nitrogen and stirred for about 7 minutes before adding 10 mL of a CH$_2$Cl$_2$ solution of 4-chromanone (0.296 g, 1.99 mmol). After the reaction mixture was stirred for 10 minutes, 10 mL of Br$_2$ (0.352 g, 2.20 mmol) was added and, the reaction mixture was stirred at room temperature for an hour. At the end of this period of time, the reaction mixture was poured into 30 mL of ice-water and, the product was extracted 3 times from the aqueous phase with EtOAc. The resultant organic phase was washed once with brine and dried under Na$_2$SO$_4$. After the solvent was evaporated, the solid formed was filtered and dried to obtain 0.361 g (1.51 mmol) of the product (93% pure) in a 74% yield.

$^1$H NMR (300 MHz, CDCl$_3$, δ): 7.90 (dd, J=2.6, 0.3 ArH, 1H,), 7.47 (dd, J=8.8, 2.5, ArH, 1H,), 6.82 (dd, J=8.8, 0.2, ArH, 1H), 4.48 (t, J=6.5, CH$_2$, 2H), 2.75 (t, J=6.5, CH$_2$, 2H).

7-Bromo-4-chromanone thiosemicarbazone (22). Into a round bottom flask containing 0.198 g of the appropriate chroman-4-one (0.336 g, 1.48 mmol), 20 mL of anhydrous methanol were added and the solution was refluxed for about 15 minutes before adding thiosemicarbazide (0.274 g, 3.01 mmol) and 38 mg of TsOH. After the reaction mixture was refluxed under nitrogen atmosphere for 12 h, the solid formed was filtered and, then purified by column chromatography (20% EtOAc/80% hex) to obtain 0.363 g (1.21 mmol) of the product in an 82% yield.

$^1$H NMR (300 MHz, CDCl$_3$, δ): 8.73 (s, NH, 1H), 8.01 (d, J=2.5, ArH, 1H), 7.38 (dd, J=8.8, 2.5, ArH, 1H), 7.35 (br s, NH$_2$, 1H), 6.83 (1H, d, J=8.7, ArH), 6.42 (br s, NH$_2$, 1H), 4.31 (t, J=6.2, CH$_2$, 2H), 2.76 (t, J=6.2, CH$_2$, 2H).

Example IV

Cathepsin L Inhibition In Vitro

Human liver cathepsin L (1 nM) was incubated in 50 mM sodium acetate buffer, pH 5.5 containing 1 mM EDTA, 2 mM DTT, 0.001% (v/v) brij 35 with potential inhibitors at 20 different concentrations (from 0.05 nM to 50 μM) at 25° C. for 5 minutes before 100 μL substrate (benzyloxycarbonyl-L-phenylalanyl-L-arginyl-7-amido-4-methylcoumarin, abbreviated as Z-FR-AMC, 50 μM in final assay condition) was added to the enzyme-inhibitor mixture; total volume was 200 μL. Controls were performed using enzyme alone, substrate alone, and enzyme with DMSO. Fluorescence excitation and emission wavelengths were 355 nm and 460 nm, respectively. Spectra were taken at 3-sec intervals for 3 minutes. IC50 values were determined by non-linear regression analysis using vo(inh)=VMAX/{1+10(logIC50−x)*Hillslope} and Prism software (GraphPad). IC50 values (nM) are summarized in Table 1 supra.

Example V

Cruzain Inhibition In Vitro

Cruzain (0.1 nM) in 100 mM sodium acetate buffer (pH 5.50) containing 5 mM DTT was preincubated for 5 min at 25° C. with inhibitor. The reaction was initiated by the addition of 20 μL of substrate, benzyloxycarbonyl-L-phenylalanyl-L-arginyl-7-amido-4-methylcoumarin (Z-Phe-Arg-AMC, Sigma, K$_m$=1.1 μM) to the enzyme-inhibitor mixture at 25° C. to give 300 μL with a final concentration of 10 μM substrate and nine to twenty concentrations of inhibitor ranging from 0.001-50000 nM. The increase in fluorescence (excitation at 355 nM and emission at 460 nM) upon release of 7-amino-4-methylcoumarin was recorded for three min with a spectrofluorimeter (Jobin Yvon-SPEX Instruments, fluoro-MAX-2). Inhibitor stock solutions were prepared in DMSO, and serial dilutions were made in DMSO to give a final concentration of 0.7% DMSO in the assay. Controls were performed using enzyme alone, substrate alone, and enzyme with DMSO. IC$_{50}$ values were determined by non-linear regression analysis using $v_{o(inh)}=V_{MAX}/\{1+10^{(X-logIC50)Hillslope}\}$ and Prism software (GraphPad). IC50 values (nM) are summarized in Table 1 supra.

Example VI

Inhibition of Activated Cathepsin L

A prostrate carcinoma derived cell line (DU-145) was maintained in free phenol red DMEM supplemented with 10% fetal bovine serum, 1% glutamine, 1% glutamax, 1% Penicillin-Streptomycin and 1 mM sodium pyruvate, at 37° C. in an atmosphere of 95% air/5% CO$_2$. DU145 was plated at 4×10$^6$ cells/10 cm Petri dish for dense, super confluent density. These cultures were incubated for 3 days before collection. Twenty-four hours prior to harvesting, cells were fed with serum-free media or serum-free media containing inhibitors at a final concentration of 20 µM.

On the day of harvesting, the serum-free medium was collected for assay of Cathepsin L activity secreted in the medium. The cells were rinsed in cold PBS (pH 7.2) and collected in cold PBS containing 0.5 M EDTA. The cells were lysed using a Sonicator (Misonix 3000) at medium setting with pauses at 0° C. for temperature equilibration. Then the homogenate was centrifuged at 13,000×g for 20 min and the supernatant saved. Both, cathepsin L and cathepsin B secreted in the medium and contained in the cell supernatant were activated in 50 mM sodium acetate buffer containing 1 mM EDTA, 2 mM DTT, and 0.001% (v/v) brij 35 (pH 5.5) for 90 min and 30 min respectively at 25° C. before 100 µL substrate (benzyloxycarbonyl-L-phenylalanyl-L-arginyl-7-amido-4-methylcoumarin, abbreviated as Z-FR-AMC, 50 µM in final assay condition) was added. Fluorescence was measured in a Fluoro Max 2 (Jobin Yvon) spectrofluorometer at an excitation wavelength of 355 nm and an emission wavelength of 460 nm. The substrate is hydrolyzed by cathepsin L and to a smaller extent by cathepsin B, therefore the activity is referred to as cathepsin L+B activity. Data analysis was performed using Prism software (GraphPad version 4).

Data corresponding to cathepsin L activity (after activation) in cell conditioned media in the presence of Compound 14 (20 µM) is summarized in Table 3 below.

TABLE 3

| Sample ID | cps | activity µM/s |
|---|---|---|
| 14a | 722.5 | 1.86E-04 |
| 14b | 641.2 | 1.65E-04 |
| 14c | 495 | 1.27E-04 |
| control | 5848 | 1.50E-03 |

Data corresponding to cathepsin L activity (after activation) in cell conditioned media in the presence of Compound 27 (20 µM) is summarized in Table 4 below.

TABLE 4

| Sample ID | cps | activity µM/s |
|---|---|---|
| 27a | 393.7 | 1.01E-04 |
| 27b | 367.5 | 9.46E-05 |
| 27c | 381.1 | 9.81E-05 |
| control | 5848 | 1.50E-03 |

Data corresponding to cathepsin L activity (after activation) in cell lysates preincubated for 24 h with Compound 14 and following the removal of media is summarized in Table 5 below.

TABLE 5

| Sample ID | cps | activity µM/s |
|---|---|---|
| 14a | 6259 | 1.61E-03 |
| 14b | 5608 | 1.44E-03 |
| 14c | 5003 | 1.29E-03 |
| control | 26950 | 6.93E-03 |

Data corresponding to cathepsin L activity (after activation) in cell lysates preincubated for 24 h with Compound 27 and following the removal of media is summarized in Table 6 below.

TABLE 6

| Sample ID | cps | activity µM/s |
|---|---|---|
| 27a | 11990 | 3.08E-03 |
| 27b | 9918 | 2.55E-03 |
| 27c | 10690 | 2.75E-03 |
| control | 26950 | 6.93E-03 |

The invention claimed is:

1. A method of inhibiting a cathepsin B or cathepsin L, comprising contacting in vitro said cathepsin with a compound of Formula I or a pharmaceutically acceptable salt, enantiomer, stereoisomer, rotamer, tautomer, diastereomer, or racemate thereof,

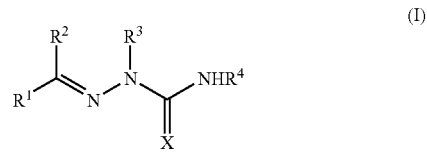

(I)

wherein said cathepsin is inhibited and
R$^1$ and R$^2$ are each, independently, selected from the group consisting of substituted or unsubstituted phenyl;
R$^3$ is selected from the group consisting of H, and substituted or unsubstituted lower alkyl; and
R$^4$ is a member selected from H and substituted or unsubstituted lower alkyl; and
X is O or S.

2. The method of claim 1, wherein R$^1$ and R$^2$ are each, independently,

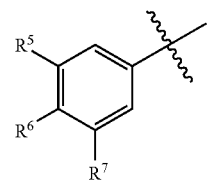

wherein
R$^5$, R$^6$, and R$^7$ are each, independently, selected from the group consisting of H, substituted or unsubstituted alkyl, substituted or unsubstituted aryl, substituted or unsubstituted heteroaryl, haloalkyl, alkoxy, NO$_2$, NH$_2$, N-acyl, OH and halo.

3. The method of claim 2, wherein R$^5$, R$^6$ and R$^7$ are each, independently, selected from the group consisting of H, halo and haloalkyl.

4. The method of claim 3, wherein halo is Br.

5. The method of claim 2, wherein R$^5$, R$^6$ and R$^7$ are each, independently, selected from the group consisting of NO$_2$, NH$_2$, OH and halo.

6. The method of claim 5, wherein halo is Br.

7. The method of claim 1, wherein R$^3$ is H.

8. The method of claim 1, wherein X is S.

9. The method of claim 1, wherein R$^4$ is H.

10. The method of claim 1, wherein the compound of Formula I is a compound selected from the group selected from the group consisting of:

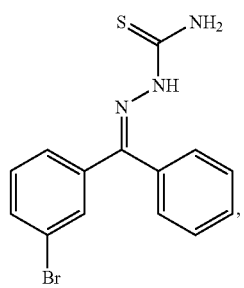
13

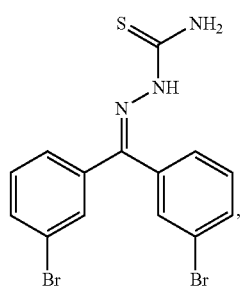
14

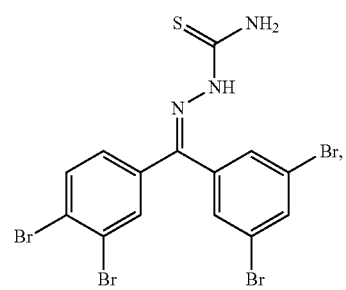
61

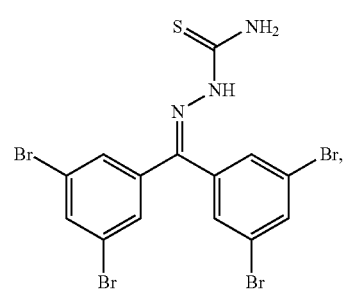
62

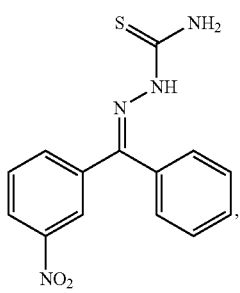
63

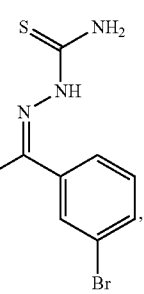
64

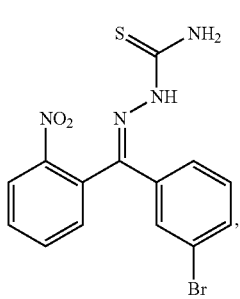
65

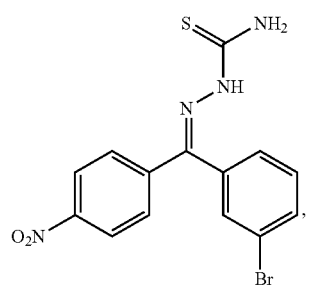
66

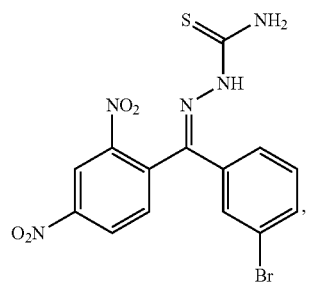
67

-continued

68

[Chemical structure: 6-fluoro-thiochroman-4-one 1,1-dioxide thiosemicarbazone]

71

[Chemical structure: (3,5-dibromophenyl)(3-bromophenyl)methanone thiosemicarbazone]

72

[Chemical structure: (3,5-dibromophenyl)(3,4-dibromophenyl)methanone thiosemicarbazone]

73

[Chemical structure: (3-aminophenyl)(3-bromophenyl)methanone thiosemicarbazone]

74

[Chemical structure: (3-hydroxyphenyl)(3-bromophenyl)methanone thiosemicarbazone], and -continued

75

[Chemical structure: (3-N-acylaminophenyl)(3-bromophenyl)methanone thiosemicarbazone].

11. The method of claim 1, wherein the compound of Formula I is

14

[Chemical structure: bis(3-bromophenyl)methanone thiosemicarbazone].

12. A method of treating prostate or breast cancer, said method comprising administering to a subject in need thereof a sufficient amount of a pharmaceutical composition comprising a compound of Formula I or a pharmaceutically acceptable salt, enantiomer, stereoisomer, rotamer, tautomer, diastereomer, or racemate thereof, $$\underset{R^1}{\overset{R^2}{\diagdown}}\!\!=\!\!N\!\!-\!\!\underset{R^3}{\overset{}{N}}\!\!-\!\!\underset{X}{\overset{}{C}}\!\!-\!\!NHR^4 \quad (I)$$

wherein
 $R^1$ and $R^2$ are each, independently, selected from the group consisting of substituted or unsubstituted phenyl;
 $R^3$ is selected from the group consisting of H, and substituted or unsubstituted lower alkyl; and
 $R^4$ is a member selected from H and substituted or unsubstituted lower alkyl; and
 X is O or S.

13. The method of claim 12, wherein the subject is human.

14. The method of claim 12, wherein $R^1$ and $R^2$ are each, independently,

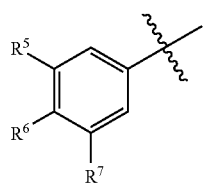

wherein

R[5], R[6], and R[7] are each, independently, selected from the group consisting of H, substituted or unsubstituted alkyl, substituted or unsubstituted aryl, substituted or unsubstituted heteroaryl, haloalkyl, alkoxy, NO$_2$, NH$_2$, N-acyl, OH and halo.

15. The method of claim 12, wherein R[5], R[6] and R[7] are each, independently, selected from the group consisting of H, halo and haloalkyl.

16. The method of claim 12, wherein R[5], R[6] and R[7] are each, independently, selected from the group consisting of NO$_2$, NH$_2$, OH and halo.

17. The method of claim 12, wherein R[3] is H.

18. The method of claim 12, wherein X is S.

19. The method of claim 12, wherein the compound of Formula I is a compound selected from the group selected from the group consisting of:

13
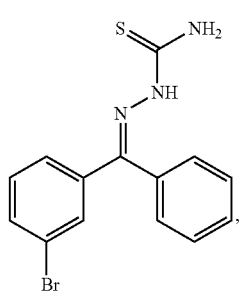

14
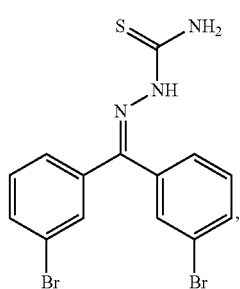

61
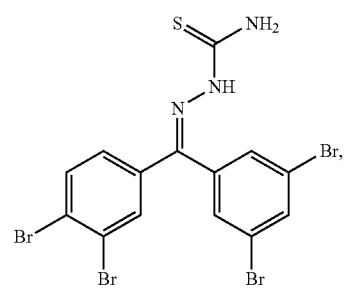

-continued

62
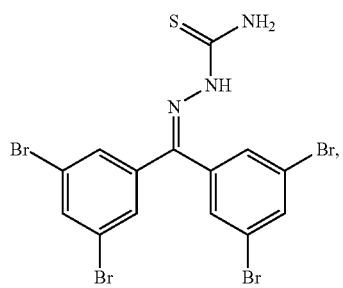

63
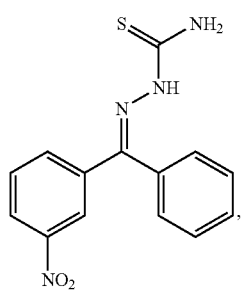

64
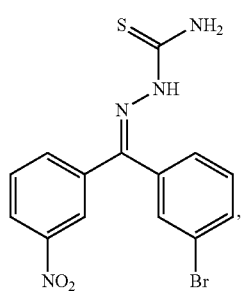

65
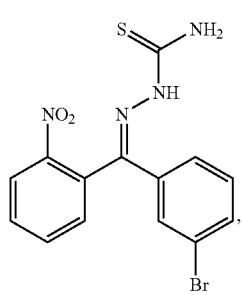

66
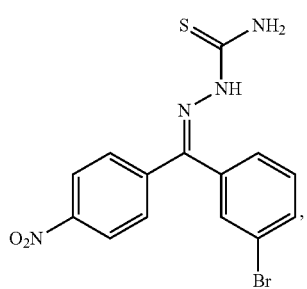

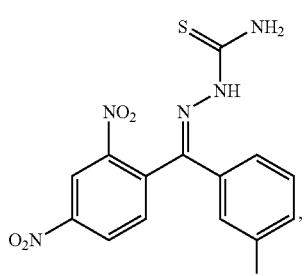
67
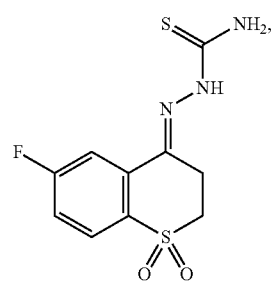
68
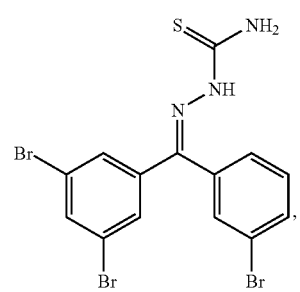
71
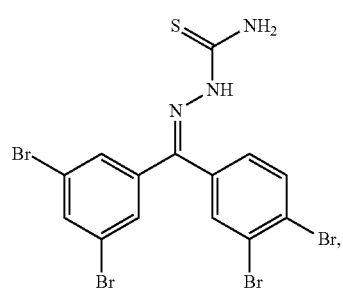
72
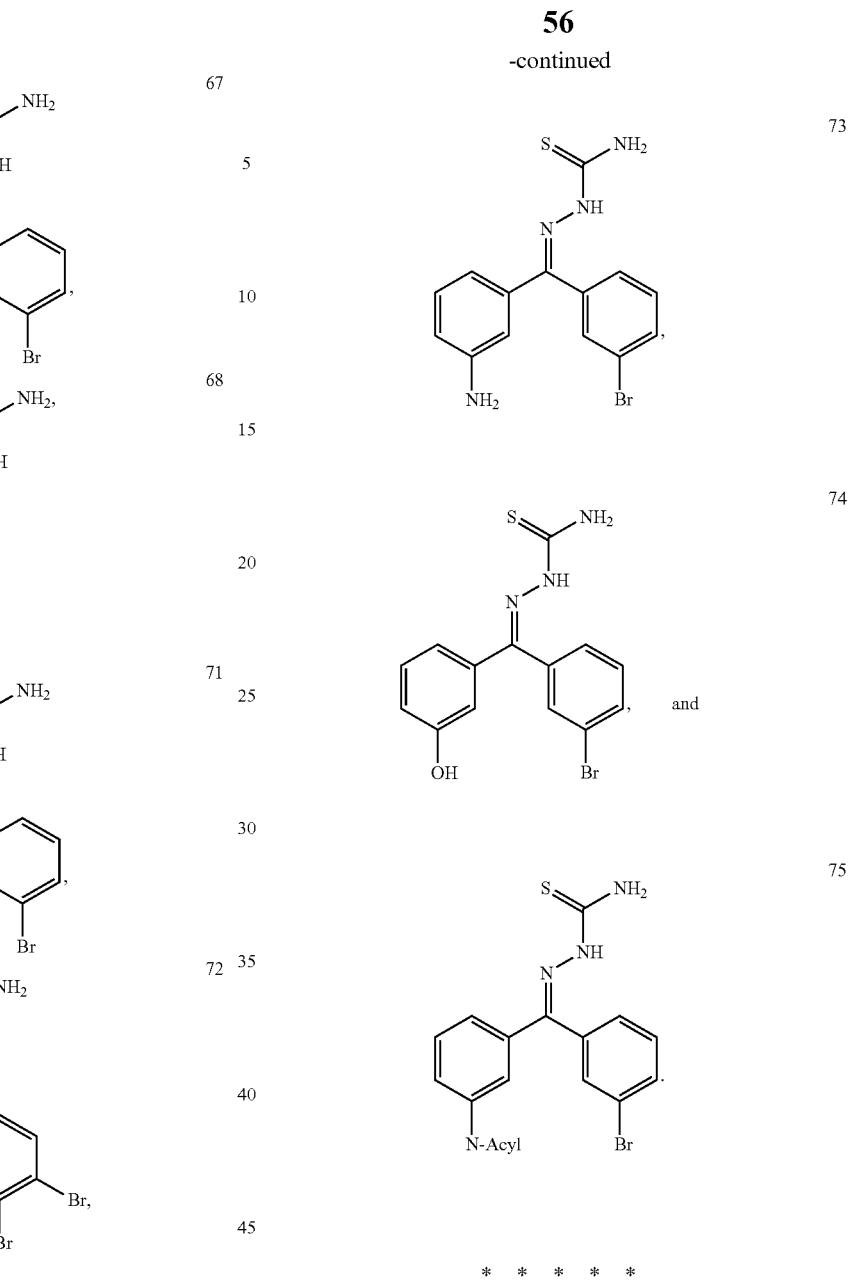
* * * * *